United States Patent
Kimura et al.

(10) Patent No.: US 9,801,843 B2
(45) Date of Patent: Oct. 31, 2017

(54) SELF-EMULSIFYING COMPOSITION OF ω3 FATTY ACID

(71) Applicant: MOCHIDA PHARMACEUTICAL CO., LTD., Tokyo (JP)

(72) Inventors: Shigeru Kimura, Tokyo (JP); Hiromitsu Ito, Tokyo (JP); Hirosato Fujii, Tokyo (JP); Motoo Yamagata, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/905,520

(22) PCT Filed: Jul. 17, 2014

(86) PCT No.: PCT/JP2014/069115
§ 371 (c)(1),
(2) Date: Jan. 15, 2016

(87) PCT Pub. No.: WO2015/008849
PCT Pub. Date: Jan. 22, 2015

(65) Prior Publication Data
US 2016/0151319 A1    Jun. 2, 2016

(30) Foreign Application Priority Data

Jul. 18, 2013 (JP) .................................. 2013-149645

(51) Int. Cl.
| | |
|---|---|
| *A61K 9/107* | (2006.01) |
| *A61K 47/44* | (2017.01) |
| *A61Q 19/00* | (2006.01) |
| *A61K 31/202* | (2006.01) |
| *A61K 31/232* | (2006.01) |
| *A61K 47/26* | (2006.01) |
| *A61K 9/48* | (2006.01) |
| *A61K 47/10* | (2017.01) |
| *A61K 47/14* | (2017.01) |
| *A23L 29/10* | (2016.01) |
| *A23L 33/115* | (2016.01) |

(52) U.S. Cl.
CPC ............ *A61K 31/202* (2013.01); *A23L 29/10* (2016.08); *A23L 33/115* (2016.08); *A61K 9/1075* (2013.01); *A61K 9/4858* (2013.01); *A61K 31/232* (2013.01); *A61K 47/10* (2013.01); *A61K 47/14* (2013.01); *A61K 47/26* (2013.01)

(58) Field of Classification Search
CPC ...... A61K 47/44; A61K 9/107; A61K 9/0014; A61Q 19/00
See application file for complete search history.

(56) References Cited

U.S. PATENT DOCUMENTS

2012/0065264 A1    3/2012    Fujii et al.

FOREIGN PATENT DOCUMENTS

| JP | 2008-516890 A | 5/2008 |
|---|---|---|
| JP | 2011-012003 A | 1/2011 |
| JP | 2012-519728 A | 8/2012 |
| JP | 2012-180337 A | 9/2012 |
| WO | WO 2006/017692 A2 | 2/2006 |
| WO | WO 2010/103402 A1 | 9/2010 |
| WO | WO 2010/119319 A1 | 10/2010 |
| WO | WO 2010/134614 A1 | 11/2010 |
| WO | WO 2011/047259 A1 | 4/2011 |
| WO | WO 2015/053379 A1 | 4/2015 |

OTHER PUBLICATIONS

International Search Report issued in PCT/JP2014/069115, mailed on Oct. 7, 2014.
Ratanabanangkoon et al., "A high-throughput approach towards a novel formulation of fenofibrate in omega-3 oil", European Journal of Pharmaceutical Sciences, 2008, vol. 33, pp. 351-360.
Written Opinion issued in PCT/JP2014/069115, mailed on Oct. 7, 2014.
Extended European Search Report, dated Feb. 13, 2017, for European Application No. 14826392.4.
Lawrence, "Polyoxyethylene Sorbitan Fatty Acid Esters," Handbook of Pharmaceutical Excipients, Fifth Edition, 2006, pp. 580-584 (Total 6 pages), XP-2765740.

*Primary Examiner* — Tracy Liu
(74) *Attorney, Agent, or Firm* — Birch, Stewart, Kolasch & Birch, LLP

(57) ABSTRACT

A self-emulsifying composition contains: 70 to 90% by weight in total of one or more compounds selected from the group consisting of ω3 polyunsaturated fatty acids and their pharmaceutically acceptable salts and esters; 1 to 29% by weight of an emulsifying agent selected from among a polyoxyethylene sorbitan fatty acid ester, a sorbitan fatty acid ester, a glycerin fatty acid ester and a polyoxyl castor oil; and 0.5 to 6% by weight of water when the composition is defined to be 100% by weight as a whole. The self-emulsifying composition is excellent in self-emulsifying property, composition dispersibility, emulsion stability, and absorbability, is free from ethanol and polyhydric alcohols or only has such an alcohol added thereto at a reduced concentration, and is useful for foods and pharmaceuticals.

12 Claims, No Drawings

SELF-EMULSIFYING COMPOSITION OF ω3 FATTY ACID

TECHNICAL FIELD

This invention provides a self-emulsifying composition containing at least one member selected from the group consisting of ω3 polyunsaturated fatty acids and their pharmaceutically acceptable salts and esters. This invention also provides a pharmaceutical product using such a composition, and production and application methods thereof.

BACKGROUND ART

Known ω3 polyunsaturated fatty acids (hereinafter abbreviated as ω3 PUFA) include α-linolenic acid, eicosapentaenoic acid (hereinafter abbreviated as EPA), and docosahexaenoic acid (hereinafter abbreviated as DHA). Since the ω3 PUFA and pharmaceutically acceptable salts and esters thereof have actions such as anti-arteriosclerosis action, platelet aggregation suppressive action, blood lipid lowering action, anti-inflammatory action, carcinostatic action, and central action, they are blended in various food products, and commercially sold in the form of health food and medical and pharmaceutical products.

Ethyl eicosapentaenoate ester (hereinafter abbreviated as EPA-E) is commercially sold in Japan as an oral therapeutic agent for ameliorating ulcer, pain, and coldness associated with arteriosclerosis obliterans as well as hyperlipidemia (product name Epadel, Mochida Pharmaceutical Co., Ltd.). When EPA-E is orally administered under fasting, increase in plasma EPA concentration is smaller than the case of the oral administration after the meal conceivably because absorption of the EPA-E requires secretion of bile acid and food components as a carrier. Accordingly, Epadel is instructed to be orally administered immediately after the meal (see Non-Patent Literature 1).

However, dosage method or drug compliance has become a problem for those people not taking breakfast with the recent change in the life style, patients who can only take meals at a reduced amount, patients who can only take a fluid diet (milk, rice broth, starch gruel, egg, soup, juice, or oral nutritional supplement), patients with reduced absorption ability of the intestinal tract (for example, elderly, patients of intestinal disease, patients after intestinal surgery, terminal cancer patients, and patients taking a lipase inhibitor), or patients who are unable to take meals such as those after the cerebral infarction.

Recent attention is being drawn to the relationship of the condition where the serum triglyceride (hereafter abbreviated as TG) level is abnormally increased after meals while being normal upon fasting, or non-fasting hypertriglyceridemia with a prolongation of such abnormal increase, to coronary artery disease, and it is desired to develop an ω3 PUFA preparation rapidly absorbable even if administered before meals and capable of suppressing the increase in serum TG level after meals.

A self-emulsifying preparation which does not contain water in the preparation and which is readily dispersible and self-emulsifying when brought into contact with water has been reported (see Patent Literature 1 and Non-Patent Literature 4). This preparation contains an ω3 PUFA and fenofibrate as its effective components, ethanol, and a surfactant.

These compositions contain ethanol as a component added for improving the dissolution of the fenofibrate. However, volatilization of the ethanol is associated with the risk of capsule deformation and bubble inclusion in the capsule, damages in the quality such as capsule deformation and cracks, as well as denaturing of the content in the capsule such as cloudiness and separation. In addition, use of a preparation containing such composition should be difficult if not impossible for patients intolerable for the alcohol (ethanol).

A self-emulsifying composition containing ethanol and polyhydric alcohols in addition to the ω3 PUFA and a surfactant which is capable of forming a dispersion having a small or very small average particle size when brought in contact with water is also reported (Patent Literature 2).

With regard to self-emulsifying compositions having a low ethanol content, a self-emulsifying composition comprising an ω3 PUFA, an emulsifier having a hydrophile lipophile balance (hereinafter abbreviated as HLB) of at least 10, lecithin, and a polyhydric alcohol such as propylene glycol or glycerin which has high self-emulsifying property, oral fasting absorbability and absorption speed has been reported (Patent Literature 3).

When a composition containing a co-solvent such as a polyhydric alcohol is encapsulated in a capsule, the co-solvent moves to the capsule film to cause denaturing of the composition as well as capsule deformation due to the softening of the capsule (Patent Literature 4).

Self-emulsifying compositions, as generally containing larger amounts of emulsifiers and, accordingly, being increased in total amount, are liable to cause inflammation of the gastrointestinal tract or have a reduced content per capsule of the biologically active component dissolved in oil component (Patent Literature 5). Accordingly, the emulsifier used in the self-emulsifying composition is preferably the one which is non-toxic or less-toxic even in the case of continuous administration, and the emulsifier is preferably used at a low content.

In view of compliance, amount of the emulsifier and alcohols incorporated should be minimized also in consideration of reducing the size of the preparation because amount of the preparation that has to be taken per administration increases with the increase in the amount of the components other than the ω3 PUFA in the self-emulsifying composition since predetermined amount of the ω3 should be taken per administration.

CITATION LIST

Patent Literatures

Patent Literature 1: JP 2008-516890 A
Patent Literature 2: JP 2012-519728 A
Patent Literature 3: WO 2010/134614
Patent Literature 4: JP 2011-12003 A
Patent Literature 5: JP 2012-180337 A

Non-Patent Literatures

Non-Patent Literature 1: Epadel S (Drug Interview Form), Mochida Pharmaceutical Co., Ltd., June, 2012
Non-Patent Literature 2: "Guideline for Diagnosis and Prevention of Atherosclerotic Cardiovascular Diseases, 2007 Edition" edited by Japan Atherosclerosis Society and published by Kyowa Kikaku Ltd., Apr. 25, 2007
Non-Patent Literature 3: Diabetes, vol. 57, no. 9, 2382-2392, 2008
Non-Patent Literature 4: European Journal of Pharmaceutical Sciences, vol. 33, 351-360, 2008

Non-Patent Literature 5: "2007 Dictionary of Drug Additives" edited by International Pharmaceutical Excipients Council Japan and published by Yakuji Nippo Ltd., Jul. 25, 2007

SUMMARY OF INVENTION

Technical Problems

There is a demand for a preparation wherein ethanol and polyhydric alcohols added to the self-emulsifying composition have been reduced.

There is also a demand for a preparation wherein emulsifier added to the self-emulsifying composition has been reduced.

There is also a demand for a preparation wherein content of the ω3 PUFA in the self-emulsifying composition has been increased.

There is also a demand for a self-emulsifying composition which shows excellent drug compliance.

There is also a demand for a self-emulsifying composition which is free from denaturing such as cloudiness and separation and which retains the good appearance during its storage at room temperature, and also, at low temperature and high temperature environments since use of the self-emulsifying composition as a drug may involve storage in cold district and other environments.

There is also a demand for a self-emulsifying composition wherein the composition has stable quality.

There is also a demand for a preparation wherein the self-emulsifying composition has been encapsulated.

There is also a demand for a preparation wherein softening of the capsule film after the encapsulation of the self-emulsifying composition is suppressed so that the capsulated preparation is not deformed.

Accordingly, an object of the present invention is to provide a self-emulsifying composition which has realized one or more of the demands as described above. Another object of the present invention is to provide a preparation encapsulating such composition.

Solution to Problems

In view of the problems as described above, the inventors of the present invention made an intensive investigation on the components which would be substitutes for the ethanol and the polyhydric alcohols, and found that a predetermined amount of water is useful in improving the compatibility of the self-emulsifying composition.

The inventors also found that the content of the emulsifying agent can be further reduced, and a self-emulsifying composition having a high content of the ω3 PUFA was thereby completed. The present invention has been completed on the basis of such findings.

The composition of the present invention is a composition which exhibits excellent properties with regard to at least one of the problems as described above.

Accordingly, a first aspect of the present invention is the self-emulsifying composition as described below.

(1-1) A self-emulsifying composition comprising, when the self-emulsifying composition is defined to be 100% by weight as a whole,
  a) 70 to 90% by weight of at least one compound selected from the group consisting of ω3 polyunsaturated fatty acids and their pharmaceutically acceptable salts and esters,
  b) 0.5 to 6% by weight of water, and
  c) 1 to 29% by weight of an emulsifying agent including either
    i) a polyoxyethylene sorbitan fatty acid ester or
    ii) at least two members selected from the group consisting of a sorbitan fatty acid ester, a glycerin fatty acid ester and a polyoxyethylene castor oil, or
  1 to 29% by weight of an emulsifying agent including
    i) a polyoxyethylene sorbitan fatty acid ester and
    ii) at least one member selected from the group consisting of a sorbitan fatty acid ester, a glycerin fatty acid ester and a polyoxyethylene castor oil, wherein
  d) content of ethanol and/or polyhydric alcohol is up to 4% by weight of the whole composition.

(1-2) A self-emulsifying composition comprising, when the self-emulsifying composition is defined to be 100% by weight as a whole,
  a) 70 to 90% by weight of at least one compound selected from the group consisting of ω3 polyunsaturated fatty acids and their pharmaceutically acceptable salts and esters,
  b) 0.5 to 6% by weight of water, and
  c) 1 to 29% by weight of an emulsifying agent including either
    i) a polyoxyethylene sorbitan fatty acid ester or
    ii) at least two members selected from the group consisting of a sorbitan fatty acid ester, a glycerin fatty acid ester and a polyoxyethylene castor oil, or
  1 to 29% by weight of an emulsifying agent including
    i) a polyoxyethylene sorbitan fatty acid ester and
    ii) at least one member selected from the group consisting of a sorbitan fatty acid ester, a glycerin fatty acid ester and a polyoxyethylene castor oil, wherein
  d) content of ethanol is up to 4% by weight of the whole composition, and
  e) content of polyhydric alcohol is up to 4% by weight of the whole composition.

(1-3) A self-emulsifying composition according to (1-1) or (1-2), wherein the polyoxyethylene sorbitan fatty acid ester is at least one member selected from the group consisting of polyoxyethylene (20) sorbitan monolaurate, polyoxyethylene (20) sorbitan monopalmitate, polyoxyethylene (20) sorbitan monostearate, polyoxyethylene (20) sorbitan tristearate, polyoxyethylene (20) sorbitan monoisostearate, polyoxyethylene (20) sorbitan monooleate, and polyoxyethylene (20) sorbitan trioleate.

(1-4) A self-emulsifying composition according to any one of (1-1) to (1-3), wherein the sorbitan fatty acid ester is at least one member selected from the group consisting of sorbitan monolaurate, sorbitan monooleate, sorbitan monopalmitate, sorbitan trioleate and sorbitan sesquioleate.

(1-5) A self-emulsifying composition according to any one of (1-1) to (1-4), wherein the glycerin fatty acid ester is at least one member selected from the group consisting of glyceryl monooleate, glyceryl monostearate, decaglyceryl monooleate, decaglyceryl monolaurate, decaglyceryl trioleate, decaglyceryl pentaoleate and tetraglyceryl monooleate.

(1-6) A self-emulsifying composition according to any one of (1-1) to (1-5), wherein the polyhydric alcohol is propylene glycol or glycerin.

(1-7) A self-emulsifying composition according to any one of (1-1) to (1-5), wherein the composition contains 0 to 4% by weight of the polyhydric alcohol.

(1-8) A self-emulsifying composition according to any one of (1-1) to (1-5), wherein the composition does not contain more than 4% by weight of the polyhydric alcohol.

(1-9) A self-emulsifying composition according to any one of (1-1) to (1-8), wherein the content of the polyhydric alcohol in the composition is up to 1% by weight.

(1-10) A self-emulsifying composition according to any one of (1-1) to (1-8), wherein the composition contains 0 to 1% by weight of the polyhydric alcohol.

(1-11) A self-emulsifying composition according to any one of (1-1) to (1-8), wherein the composition does not contain more than 1% by weight of the polyhydric alcohol.

(1-12) A self-emulsifying composition according to any one of (1-1) to (1-11), wherein the composition contains substantially no polyhydric alcohol.

(1-13) A self-emulsifying composition according to any one of (1-1) to (1-12), wherein the content of the ethanol in the composition is up to 4% by weight.

(1-14) A self-emulsifying composition according to any one of (1-1) to (1-12), wherein the composition contains 0 to 4% by weight of the ethanol.

(1-15) A self-emulsifying composition according to any one of (1-1) to (1-12), wherein the composition does not contain more than 4% by weight of the ethanol.

(1-16) A self-emulsifying composition according to any one of (1-1) to (1-15), wherein the composition contains substantially no ethanol.

(1-17) A self-emulsifying composition according to any one of (1-1) to (1-16), wherein the ω3 PUFAs and their pharmaceutically acceptable salts and esters include at least one member selected from the group consisting of EPA, DHA, and their pharmaceutically acceptable salts and esters.

(1-18) A self-emulsifying composition according to any one of (1-1) to (1-17), wherein the esters of the ω3 PUFAs are ethyl esters or triglyceride esters.

(1-19) A self-emulsifying composition according to any one of (1-1) to (1-18), wherein EPA-E or ethyl DHA ester (hereinafter abbreviated as DHA-E) is selected from among the ω3 PUFAs and their pharmaceutically acceptable salts and esters.

(1-20) A self-emulsifying composition according to any one of (1-1) to (1-19), which contains at least one member selected from the group consisting of EPA, DHA, and their pharmaceutically acceptable salts and esters as its effective component.

(1-21) A self-emulsifying composition according to any one of (1-1) to (1-20), which contains EPA-E and/or DHA-E as its effective component.

(1-22) A self-emulsifying composition according to any one of (1-1) to (1-21), which contains EPA-E as its effective component.

(1-23) A self-emulsifying composition according to any one of (1-1) to (1-22), wherein the composition contains less than 3 parts by weight of lecithin in relation to 100 parts by weight of the at least one compound selected from the group consisting of ω3 PUFAs and their pharmaceutically acceptable salts and esters.

(1-24) A self-emulsifying composition according to any one of (1-1) to (1-23), wherein the composition contains no lecithin.

(1-25) A self-emulsifying composition according to (1-23), wherein the lecithin is at least one member selected from the group consisting of soybean lecithin, zymolytic soybean lecithin, hydrogenated soybean lecithin, and egg yolk lecithin.

(1-26) A self-emulsifying composition according to any one of (1-1) to (1-25), which has a transparent appearance when allowed to stand.

(1-27) A self-emulsifying composition according to any one of (1-1) to (1-26), which has a non-separated or non-cloudy appearance when allowed to stand.

(1-28) A self-emulsifying composition according to any one of (1-1) to (1-27), which has a transparent appearance when stored in the environment of 5° C. or 40° C. for 12 hours.

(1-29) A self-emulsifying composition according to any one of (1-1) to (1-28), which has a non-separated or non-cloudy appearance when stored in the environment of 5° C. or 40° C. for 12 hours.

(1-30) A self-emulsifying composition according to any one of (1-1) to (1-29), which is excellent in at least one out of self-emulsifying property, composition dispersibility, and emulsion stability.

(1-31) A self-emulsifying composition according to any one of (1-1) to (1-30), which spontaneously emulsifies when 10 μL of the composition is added dropwise to 5 mL of purified water or first fluid for dissolution test of Japanese Pharmacopeia at 37° C.

(1-32) A self-emulsifying composition according to any one of (1-1) to (1-31), which is dispersed by agitation when 10 μL of the composition is added dropwise to 5 mL of purified water or first fluid for dissolution test of Japanese Pharmacopeia at 37° C.

(1-33) A self-emulsifying composition according to any one of (1-1) to (1-32), wherein separation of the oil component does not occur when 10 μL of the composition is added dropwise to 5 mL of purified water or first fluid for dissolution test of Japanese Pharmacopeia at 37° C.

(1-34) A self-emulsifying composition according to any one of (1-1) to (1-33), wherein, when the self-emulsifying composition according to any one of (1-1) to (1-33) is orally administered to a male beagle which has been fasted for at least 18 hours in an amount corresponding to 600 mg of the at least one compound selected from the group consisting of ω3 PUFAs and their pharmaceutically acceptable salts and esters, the maximum blood ω3 PUFA concentration is at least 50 μg/mL and/or the area under the blood ω3 PUFA concentration vs time curve from zero to two hours after the administration is at least 30 μg/mL·hr, or the maximum blood ω3 PUFA concentration is at least 50 μg/mL and/or the area under the blood ω3 PUFA concentration vs time curve from zero to two hours after the administration is at least 50 μg/mL·hr, or the maximum blood ω3 PUFA concentration is at least 60 μg/mL and/or the area under the blood ω3 PUFA concentration vs time curve from zero to two hours after the administration is at least 60 μg/mL·hr, or the maximum blood ω3 PUFA concentration is at least 70 μg/mL and/or the area under the blood ω3 PUFA concentration vs time curve from zero to two hours after the administration is at least 70 μg/mL·hr, as calculated with correction by subtraction of the blood ω3 polyunsaturated fatty acid concentration before the administration of the composition.

(1-35) A self-emulsifying composition according to any one of (1-1) to (1-33), wherein, when the self-emulsifying composition according to any one of (1-1) to (1-33) is orally administered to a male crab-eating macaque which has been fasted for at least 12 hours in an amount corresponding to 45 mg/kg body weight of the at least one compound selected from the group consisting of ω3 PUFAs and their pharmaceutically acceptable salts and esters, the maximum blood ω3 PUFA concentration is at least 50 μg/mL and/or the area under the blood ω3 PUFA concentration vs time curve from zero to 12 hours after the administration is at least 400 μg/mL·hr, or the maximum blood ω3 PUFA concentration is at least 70 μg/mL and/or the area under the blood ω3 PUFA concentration vs time curve from zero to 12 hours after the administration is at least 500 µg/mL·hr, as calculated with correction by subtraction of the blood ω3 polyunsaturated fatty acid concentration before the administration of the composition.

(1-36) A self-emulsifying composition according to any one of (1-1) to (1-33), wherein, when the self-emulsifying composition according to any one of (1-1) to (1-33) is orally administered to a human before meals in an amount corresponding to 1800 mg of the at least one compound selected from the group consisting of ω3 PUFAs and their pharmaceutically acceptable salts and esters, the maximum blood ω3 PUFA concentration is at least 50 µg/mL and/or the blood ω3 PUFA concentration two hours after the administration is at least 10 µg/mL, as calculated with correction by subtraction of the blood ω3 polyunsaturated fatty acid concentration before the administration of the composition.

(1-37) A self-emulsifying composition according to any one of (1-1) to (1-33), wherein, when the self-emulsifying composition according to any one of (1-1) to (1-33) is orally administered to a human before meals in an amount corresponding to 1800 mg of the at least one compound selected from the group consisting of ω3 PUFAs and their pharmaceutically acceptable salts and esters, the maximum blood ω3 PUFA concentration is at least 10 µg/mL and/or the area under the blood ω3 PUFA concentration vs time curve from zero to 72 hours after the administration is at least 250 µg/mL·hr, as calculated with correction by subtraction of the blood ω3 polyunsaturated fatty acid concentration before the administration of the composition.

(1-38) A self-emulsifying composition comprising, when the self-emulsifying composition is defined to be 100% by weight as a whole,
  a) 70 to 90% by weight of EPA-E,
  b) 0.5 to 6% by weight of water, and
  c) 1 to 29% by weight of an emulsifying agent including either
    i) a polyoxyethylene sorbitan fatty acid ester or
    ii) at least two members selected from the group consisting of a sorbitan fatty acid ester, a glycerin fatty acid ester and a polyoxyethylene castor oil, or
  1 to 29% by weight of an emulsifying agent including
    i) a polyoxyethylene sorbitan fatty acid ester and
    ii) at least one member selected from the group consisting of a sorbitan fatty acid ester, a glycerin fatty acid ester and a polyoxyethylene castor oil, wherein
  d) content of ethanol and/or polyhydric alcohol is up to 4% by weight of the whole composition, and
  e) content of lecithin is less than 3 parts by weight in relation to 100 parts by weight of a).

(1-39) A self-emulsifying composition comprising, when the self-emulsifying composition is defined to be 100% by weight as a whole,
  a) 70 to 90% by weight of EPA-E,
  b) 0.5 to 6% by weight of water, and
  c) 1 to 29% by weight of an emulsifying agent including either
    i) a polyoxyethylene sorbitan fatty acid ester or
    ii) at least two members selected from the group consisting of a sorbitan fatty acid ester, a glycerin fatty acid ester and a polyoxyethylene castor oil, or
  1 to 29% by weight of an emulsifying agent including
    i) a polyoxyethylene sorbitan fatty acid ester and
    ii) at least one member selected from the group consisting of a sorbitan fatty acid ester, a glycerin fatty acid ester and a polyoxyethylene castor oil, wherein
  d) content of ethanol is up to 4% by weight of the whole composition,
  e) content of polyhydric alcohol is up to 4% by weight of the whole composition, and
  f) content of lecithin is less than 3 parts by weight in relation to 100 parts by weight of a).

A second aspect of the present invention is the capsulated self-emulsifying preparation as described below.

(2-1) A capsulated self-emulsifying preparation having the self-emulsifying composition according to any one of (1-1) to (1-39) encapsulated in a hard capsule and/or a soft capsule as a liquid content.

(2-2) A capsulated self-emulsifying preparation according to (2-1), which exhibits sufficient hardness immediately after its production.

(2-3) A capsulated self-emulsifying preparation according to (2-1) or (2-2), which has a hardness of 18 kgf or more immediately after its production.

(2-4) A capsulated self-emulsifying preparation according to any one of (2-1) to (2-3), which does not experience loss of its hardness of 6 kgf or more when sealed in an aluminum package and stored at 40° C. for 1 week, and then compared with the preparation before the storage.

(2-5) A capsulated self-emulsifying preparation according to any one of (2-1) to (2-4), which has a hardness of 20 kgf or more when sealed in an aluminum package and stored at 40° C. for 1 week.

(2-6) A capsulated self-emulsifying preparation according to any one of (2-1) to (2-5), which, when sealed in an aluminum package and stored at 40° C. for 1 week, retains 60% or more of its hardness before the storage.

(2-7) A preparation according to (2-1), which serves as at least one drug selected from the group consisting of therapeutic agent for dyslipidemia (hypercholesterolemia, LDL hypercholesterolemia, non-HDL hypercholesterolemia, VLDL hypercholesterolemia, HDL hypocholesterolemia, hypertriglyceridemia, apo B hyperlipoproteinemia, apo A-I hypolipoproteinemia, and so forth), therapeutic agent for postprandial hypertriglyceridemia, anti-arteriosclerosis agent, platelet aggregation suppressant, therapeutic agent for peripheral circulatory insufficiency, prophylactic agent for cardiovascular events, therapeutic agent for inflammatory disease (non-alcoholic fatty liver disease (hereafter abbreviated as NAFLD), non-alcoholic steatohepatitis (hereafter abbreviated as NASH), and so forth), progression suppressant and therapeutic agent for cognitive impairment (dementia of the Alzheimer's type, cerebrovascular dementia, mixed type of dementia, and so forth), anticancer agent, and therapeutic agent for central disease (depression, depressive condition, obsessive-compulsive disorder, social anxiety disorder, panic disorder, and so forth).

A third aspect of the present invention is the method for producing a self-emulsifying composition as described below.

(3-1) A method for producing a self-emulsifying composition, comprising the step of:
  mixing the following components a) to c) in any order while defining the self-emulsifying composition to be 100% by weight as a whole,
  a) 70 to 90% by weight of at least one compound selected from the group consisting of ω3 polyunsaturated fatty acids and their pharmaceutically acceptable salts and esters,
  b) 0.5 to 6% by weight of water, and
  c) 1 to 29% by weight of an emulsifying agent including either i) a polyoxyethylene sorbitan fatty acid ester or
ii) at least two members selected from the group consisting of a sorbitan fatty acid ester, a glycerin fatty acid ester and a polyoxyethylene castor oil, or
1 to 29% by weight of an emulsifying agent including
i) a polyoxyethylene sorbitan fatty acid ester and
ii) at least one member selected from the group consisting of a sorbitan fatty acid ester, a glycerin fatty acid ester and a polyoxyethylene castor oil, so that, in the resultant composition,
d) content of ethanol and/or polyhydric alcohol may be up to 4% by weight of the whole composition.

(3-2) A method for producing a self-emulsifying composition, comprising the step of:
mixing the following components a) to c) in any order while defining the self-emulsifying composition to be 100% by weight as a whole,
a) 70 to 90% by weight of at least one compound selected from the group consisting of ω3 polyunsaturated fatty acids and their pharmaceutically acceptable salts and esters,
b) 0.5 to 6% by weight of water, and
c) 1 to 29% by weight of an emulsifying agent including either
i) a polyoxyethylene sorbitan fatty acid ester or
ii) at least two members selected from the group consisting of a sorbitan fatty acid ester, a glycerin fatty acid ester and a polyoxyethylene castor oil, or
1 to 29% by weight of an emulsifying agent including
i) a polyoxyethylene sorbitan fatty acid ester and
ii) at least one member selected from the group consisting of a sorbitan fatty acid ester, a glycerin fatty acid ester and a polyoxyethylene castor oil, so that, in the resultant composition,
d) content of ethanol may be up to 4% by weight of the whole composition, and
e) content of polyhydric alcohol may be up to 4% by weight of the whole composition.

(3-3) A method for producing a self-emulsifying composition according to (3-1) or (3-2), further comprising the step of heating the a), b), and/or c) to a temperature of 70° C. or higher before the mixing step.

A fourth aspect of the present invention is the pharmaceutical preparation as described below for administering a self-emulsifying composition by a particular method.

(4-1) A preparation for orally administering at least one self-emulsifying composition or capsulated self-emulsifying preparation, drug or veterinary drug selected from among those according to (1-1) to (1-39), (2-1) to (2-7) and (3-1) to (3-3) under fasting or at bedtime.

(4-2) A preparation for orally administering the self-emulsifying composition or capsulated self-emulsifying preparation, drug or veterinary drug as produced by the production method according to any one of (3-1) to (3-3) under fasting or at bedtime.

(4-3) A preparation according to (4-1) or (4-2), which serves as at least one member selected from the group consisting of therapeutic agent for dyslipidemia (hypercholesterolemia, LDL hypercholesterolemia, non-HDL hypercholesterolemia, VLDL hypercholesterolemia, HDL hypocholesterolemia, hypertriglyceridemia, apo B hyperlipoproteinemia, apo A-I hypolipoproteinemia, and so forth), therapeutic agent for postprandial hypertriglyceridemia, anti-arteriosclerosis agent, platelet aggregation suppressant, therapeutic agent for peripheral circulatory insufficiency, prophylactic agent for cardiovascular events, therapeutic agent for inflammatory disease (NAFLD, NASH, and so forth), progression suppressant and therapeutic agent for cognitive impairment (dementia of the Alzheimer's type, cerebrovascular dementia, mixed type of dementia, and so forth), anticancer agent, as well as prophylactic agent, therapeutic agent and progression preventing agent for central disease (depression, depressive condition, obsessive-compulsive disorder, social anxiety disorder, panic disorder, and so forth).

(4-4) A preparation according to any one of (4-1) to (4-3), which is administered once a day.

(4-5) A method for administering and/or using the preparation according to any one of (4-1) to (4-4).

(4-6) A method for increasing the concentration of ω3 PUFA in plasma by the oral administration as stated in any one of (4-1) to (4-4).

A fifth aspect of the present invention is a method of prophylaxis, progression prevention, and therapy for at least one disease selected from the group below.

(5-1) A method of prophylaxis, progression prevention, and therapy for at least one disease selected from the group consisting of dyslipidemia (hypercholesterolemia, LDL hypercholesterolemia, non-HDL hypercholesterolemia, VLDL hypercholesterolemia, HDL hypocholesterolemia, hypertriglyceridemia, apo B hyperlipoproteinemia, apo A-I hypolipoproteinemia, and so forth), postprandial hypertriglyceridemia, arteriosclerosis, increase of platelet aggregation, peripheral circulatory insufficiency, onset of a cardiovascular event, inflammatory disease (NAFLD, NASH, and so forth), cognitive impairment (dementia of the Alzheimer's type, cerebrovascular dementia, mixed type of dementia, and so forth), cancer, and central disease (depression, depressive condition, obsessive-compulsive disorder, social anxiety disorder, panic disorder, and so forth), comprising the step of orally administering at least one self-emulsifying composition or capsulated self-emulsifying preparation, drug or veterinary drug selected from among those according to (1-1) to (1-39), (2-1) to (2-7) and (3-1) to (3-3) to a patient.

(5-2) A method according to (5-1), wherein the self-emulsifying composition or capsulated self-emulsifying preparation, drug or veterinary drug is orally administered under fasting or at bedtime.

(5-3) A method according to (5-1) or (5-2), wherein the self-emulsifying composition or capsulated self-emulsifying preparation, drug or veterinary drug is administered once a day.

A sixth aspect of the present invention is the self-emulsifying composition as described below.

(6-1) A self-emulsifying composition, wherein, when the self-emulsifying composition is orally administered to a male beagle which has been fasted for at least 18 hours in an amount corresponding to 600 mg of at least one compound selected from the group consisting of ω3 PUFAs and their pharmaceutically acceptable salts and esters, the maximum blood ω3 PUFA concentration is at least 50 μg/mL and/or the area under the blood ω3 PUFA concentration vs time curve from zero to two hours after the administration is at least 30 μg/mL·hr, or the maximum blood ω3 PUFA concentration is at least 50 μg/mL and/or the area under the blood ω3 PUFA concentration vs time curve from zero to two hours after the administration is at least 50 μg/mL·hr, or the maximum blood ω3 PUFA concentration is at least 60 μg/mL and/or the area under the blood ω3 PUFA concentration vs time curve from zero to two hours after the administration is at least 60 μg/mL·hr, or the maximum blood ω3 PUFA concentration is at least 70 μg/mL and/or the area under the blood ω3 PUFA concentration vs time curve from zero to two hours after the administration is at least 70 μg/mL·hr, as calculated with correction by subtraction of the blood ω3 polyunsaturated fatty acid concentration before the administration of the composition.

(6-2) A self-emulsifying composition, wherein, when the self-emulsifying composition is orally administered to a male crab-eating macaque which has been fasted for at least 12 hours in an amount corresponding to 45 mg/kg body weight of at least one compound selected from the group consisting of ω3 PUFAs and their pharmaceutically acceptable salts and esters, the maximum blood ω3 PUFA concentration is at least 50 μg/mL and/or the area under the blood ω3 PUFA concentration vs time curve from zero to 12 hours after the administration is at least 400 μg/mL·hr, or the maximum blood ω3 PUFA concentration is at least 70 μg/mL and/or the area under the blood ω3 PUFA concentration vs time curve from zero to 12 hours after the administration is at least 500 μg/mL·hr, as calculated with correction by subtraction of the blood ω3 polyunsaturated fatty acid concentration before the administration of the composition.

(6-3) A self-emulsifying composition, wherein, when the self-emulsifying composition is orally administered to a human before meals in an amount corresponding to 1800 mg of at least one compound selected from the group consisting of ω3 PUFAs and their pharmaceutically acceptable salts and esters, the maximum blood ω3 PUFA concentration is at least 50 μg/mL and/or the blood ω3 PUFA concentration two hours after the administration is at least 10 μg/mL, as calculated with correction by subtraction of the blood ω3 polyunsaturated fatty acid concentration before the administration of the composition.

(6-4) A self-emulsifying composition, wherein, when the self-emulsifying composition is orally administered to a human before meals in an amount corresponding to 1800 mg of at least one compound selected from the group consisting of ω3 PUFAs and their pharmaceutically acceptable salts and esters, the maximum blood ω3 PUFA concentration is at least 10 μg/mL and/or the area under the blood ω3 PUFA concentration vs time curve from zero to 72 hours after the administration is at least 250 μg/mL·hr, as calculated with correction by subtraction of the blood ω3 polyunsaturated fatty acid concentration before the administration of the composition.

Advantageous Effects of Invention

The self-emulsifying composition of the present invention contains a small amount of water instead of the ethanol and the polyhydric alcohol in its composition. Compatibility of the composition improves by such composition, and amount of the emulsifier used can also be reduced, and accordingly, safety for animals (including human) is thereby improved. In addition, the ω3 PUFA will be included at a higher content, and this enables reduction in the amount of emulsifier used, and compliance is thereby improved.

Inclusion of the water in the composition also enables a composition without or with minimized use of the ethanol or the polyhydric alcohols, and hence, prevention of the softening of the capsule film, and deformation of the capsule.

The self-emulsifying composition of the present invention is excellent in at least one out of compatibility (appearance), self-emulsifying property, composition dispersibility, emulsion stability, and absorbability, and it will be rapidly absorbed even if administered before meals or after the intake of low fat diet to suppress the increase in serum TG after meals or, if administered at bedtime, it will prevent the essential fatty acid deficiency in a subject taking a lipase inhibitor.

In addition, the inventive self-emulsifying composition is free from separation and cloudiness, that is to say, maintains good appearance when stored at room temperature, a lower temperature (e.g., 5° C.) or a higher temperature (e.g., 40° C.). Preferably, the composition is free from separation and cloudiness and thus maintains good appearance under any two out of the above temperature conditions, more preferably under all three conditions.

The self-emulsifying composition of the present invention has at least one, preferably at least two, and more preferably all of the advantageous characters as described above.

DESCRIPTION OF EMBODIMENTS

Next, the present invention is described in detail.

The present invention relates to a self-emulsifying composition comprising 70 to 90% by weight in total of at least one compound selected from the group consisting of ω3 polyunsaturated fatty acids and their pharmaceutically acceptable salts and esters and 1 to 29% by weight of a particular emulsifying agent and having low or no content of ethanol or polyhydric alcohol, a capsulated self-emulsifying preparation having such self-emulsifying composition encapsulated as a content, and a pharmaceutical preparation, a production method and a method of use thereof.

In the present invention, "ω3 PUFA" is a fatty acid having a plurality of carbon-carbon double bonds in the molecule, and the first double bond is at 3rd position from the end on the side of the methyl group. Typical examples include α-linolenic acid, EPA, DHA, eicosatrienoic acid, stearidonic acid, eicosatetraenoic acid, clupanodonic acid, tetracosapentaenoic acid, and nisinic acid. Unless otherwise specified, the terms "ω3 PUFA," "EPA," "DHA" and "fatty acid" as used in the present invention mean a ω3 PUFA, EPA, DHA and a fatty acid inclusive of pharmaceutically acceptable salts and esters thereof, respectively.

The ω3 PUFA used in the present invention may be a synthetic, semi-synthetic, natural ω3 PUFA, or a natural oil containing such ω3 PUFA. Examples of the natural ω3 PUFA include an extract from a natural oil containing an ω3 PUFA, a crudely purified natural oil containing an ω3 PUFA, and a highly purified natural oil containing an ω3 PUFA produced by a method known in the art. Exemplary semi-synthetic ω3 PUFAs include ω3 PUFAs produced by a microorganism or the like and the ω3 PUFAs or the natural ω3 PUFAs which have been subjected to a chemical treatment such as esterification or ester exchange. In the present invention, the ω3 PUFAs may be used alone or in combination of two or more.

In the present invention, EPA and DHA are the preferable examples of the ω3 PUFAs, and EPA is more preferable. Examples of the pharmaceutically acceptable salts of the ω3 PUFA include inorganic salts such as sodium salts and potassium salts, organic salts such as benzylamine salts and diethylamine salts, salts with basic amino acids such as arginine salts and lysine salts, and exemplary esters include alkyl esters such as ethyl ester, and esters such as monoglyceride, diglyceride and triglyceride. Preferable examples include ethyl ester and TG ester, and the more preferred is ethyl ester. More specifically, preferable examples include EPA-E, TG ester of EPA, DHA-E, and TG ester of DHA, and among these, the more preferred are EPA-E and DHA-E, and the most preferred is EPA-E.

The ω3 PUFA used as a starting material of the self-emulsifying composition of the present invention is not particularly limited in purity. The purity is typically such that the content of the ω3 PUFA in relation to the total fatty acid contained in the composition of the present invention could be preferably at least 50% by weight, more preferably at least 70% by weight, still more preferably at least 80% by weight, still more preferably at least 90% by weight, still more preferably at least 96.5% by weight, and most preferably at least 98% by weight. The ω3 PUFA containing EPA at a high purity, for example, the one with an EPA content of at least 50% by weight is preferable, and the content is more preferably at least 60% by weight, still more preferably at least 70% by weight, still more preferably at least 80% by weight, still more preferably at least 90% by weight, even more preferably at least 96.5% by weight, and most preferably at least 98% by weight. In other words, the composition of the present invention preferably has a high purity of ω3 PUFAs in the total fatty acid, more preferably, a high purity of EPA+DHA as ω3 PUFAs, and most preferably has EPA at such a purity that EPA is essentially associated with no DHA or merely with, for instance, less than 1.0%, preferably less than 0.5%, and more preferably less than 0.2% of DHA.

For example, when EPA-E and DHA-E are used, compositional ratio of EPA-E/DHA-E and content of (EPA-E+DHA-E) in relation to the total fatty acid are not particularly limited as long as the purity of EPA-E in the composition of the present invention is in the range as described above. However, the compositional ratio of the EPA-E/DHA-E is preferably at least 0.8, more preferably at least 1.0, and most preferably at least 1.2.

The composition of the present invention may also contain a polyunsaturated fatty acid other than the ω3 PUFA, such as linoleic acid, γ linolenic acid or dihomo-γ-linolenic acid, or a pharmaceutically acceptable salt or ester thereof. It, however, is desirable that the content of arachidonic acid or a pharmaceutically acceptable salt or ester thereof is low, preferably less than 2% by weight, and more preferably less than 1% by weight. Particularly preferred is the composition which is essentially free from arachidonic acid and pharmaceutically acceptable salts and esters thereof.

In the self-emulsifying composition of the present invention, content of the ω3 PUFA is 70 to 90% by weight, preferably 70 to 86% by weight, more preferably 72 to 85% by weight, and still more preferably 74 to 84% by weight. The ω3 PUFA may be a single ω3 PUFA or a mixture of two or more ones. If a mixture is used, the content of mixed fatty acids in the self-emulsifying composition is 70 to 90% by weight in total.

The ω3 PUFA used may be a soft capsule containing the EPA-E at a high purity (at least 96.5% by weight) (product name, Epadel; manufactured by Mochida Pharmaceutical Co., Ltd.) commercially available in Japan as a therapeutic agent for ASO and hyperlipidemia or a high purity EPA-E containing capsule (product name, VASCEPA; Amarin) commercially available in the U.S. as a therapeutic agent for hypertriglyceridemia. The ω3 PUFA used may also be a mixture of EPA-E and DHA-E, for example, Lovaza (Registered Trademark) (a soft capsule containing about 46.5% by weight of EPA-E and about 37.5% by weight of DHA-E from GlaxoSmithKline) commercially available in the U.S. as a therapeutic agent for hypertriglyceridemia or LOTRIGA (Registered Trademark) (a soft capsule containing about 46.5% by weight of EPA-E and about 37.5% by weight of DHA-E from Takeda Pharmaceutical Co., Ltd.) commercially available in Japan. It is also possible to use a mixture of EPA and DHA such as Epanova (Registered Trademark) (a soft capsule containing about 50 to 60% by weight of EPA free acid and about 15 to 25% by weight of DHA free acid from AstraZeneca) commercially available in the U.S. as a therapeutic agent for hypertriglyceridemia.

Purified fish oils may also be used for the ω3 PUFA, and uses of monoglyceride (MG), diglyceride (DG), and TG derivatives and combinations thereof as the ω3 PUFA are also preferable embodiments. Various products containing the ω3 PUFA are commercially available, for example, Incromega F2250, F2628, E2251, F2573, TG2162, TG2779, TG2928, TG3525, and E5015 (Croda International PLC, Yorkshire, England), and EPAX6000FA, EPAX5000TG, EPAX4510TG, EPAX2050TG, EPAX7010EE, K85TG, K85EE, and K80EE (Pronova Biopharma, Lysaker, Norway). These products may be purchased and used for the composition of the present invention.

In the present invention, the "polyoxyethylene sorbitan fatty acid ester" is polyoxyethylene ether of a fatty acid ester wherein a part of the hydroxy groups of anhydrous sorbitol have been esterified with a fatty acid. Various compounds with different esterifying fatty acids are commercially available, and examples include polyoxyethylene (20) sorbitan monolaurate (NIKKOL TL-10, polysorbate 20, Tween 20), polyoxyethylene (20) sorbitan monopalmitate (NIKKOL TP-10V, Polysorbate 40, Tween 40), polyoxyethylene (20) sorbitan monostearate (NIKKOL TS-10MV, polysorbate 60, Tween 60), polyoxyethylene (20) sorbitan tristearate (NIKKOL TS-30V, polysorbate 65), polyoxyethylene (20) sorbitan monoisostearate (NIKKOL TI-10V), polyoxyethylene (20) sorbitan monooleate (NIKKOL TO-10MV, polysorbate 80, Tween 80), and polyoxyethylene (20) sorbitan trioleate (NIKKOL TO-30V, polysorbate 85), and the preferred are polyoxyethylene (20) sorbitan monostearate, polyoxyethylene (20) sorbitan monooleate, and polyoxyethylene (20) sorbitan trioleate, and the more preferred is polyoxyethylene (20) sorbitan monooleate.

These may be used alone or in combination of two or more. The term "polyoxyethylene sorbitan fatty acid ester" as used in the present invention means all of such compounds.

Content of the polyoxyethylene sorbitan fatty acid ester in the self-emulsifying composition of the present invention is not particularly limited as long as the merits of the present invention are not adversely affected. The content is generally 1 to 29% by weight, preferably 5 to 20% by weight, and more preferably 7 to 15% by weight when the self-emulsifying composition is defined to be 100% by weight as a whole.

In the present invention, the "sorbitan fatty acid ester" is a compound obtained by esterifying hydroxy groups of anhydrous sorbitol with a fatty acid. Various compounds with different esterifying fatty acids are commercially available, and examples include sorbitan monolaurate (Span 20; NIKKOL SL-10; Nonion LP-20R), sorbitan monostearate (NIKKOL SS-10MV), sorbitan monooleate (Span 80; NIKKOL SO-10V), sorbitan monopalmitate (Span 40; NIKKOL SP-10V), sorbitan trioleate (NIKKOL SO-30) and sorbitan sesquioleate (Span 83; NIKKOL SO-15MV; Nonion OP-83R), with sorbitan monolaurate, sorbitan monooleate and sorbitan sesquioleate, among others sorbitan monolaurate, being preferred. These may be used alone or in combination of two or more. The term "sorbitan fatty acid ester" as used in the present invention means all of such compounds.

Content of the sorbitan fatty acid ester in the self-emulsifying composition of the present invention is not particularly limited as long as the merits of the present invention are not adversely affected. The content is generally 1 to 20% by weight, preferably 2 to 15% by weight, and more preferably 3 to 10% by weight when the self-emulsifying composition is defined to be 100% by weight as a whole, or 2 to 8% by weight, preferably 2 to 7% by weight, and more preferably 3 to 5% by weight when the self-emulsifying composition is defined to be 100% by weight as a whole.

In the present invention, the "glycerin fatty acid ester" is an ester of a fatty acid and glycerin or polyglycerin and derivatives thereof (including glycerin fatty acid ester, acetic and fatty acid esters of glycerol, lactic and fatty acid esters of glycerol, citric and fatty acid esters of glycerol, succinic and fatty acid esters of glycerol, diacetyl tartaric and fatty acid esters of glycerol, glycerin acetic acid ester, polyglycrin fatty acid ester, and polygrycelin condensed ricinoleic acid ester).

Various compounds are commercially available, and examples include glyceryl monooleate (PECEOL), glyceryl monostearate (NIKKOL MGS-F50SEV, MGS-AMV, MGS-BMV), decaglyceryl monooleate (NIKKOL Decaglyn 1-OV; POEM J-0381V), decaglyceryl monolaurate (NIKKOL Decaglyn 1-L), dacaglyceryl trioleate (NIKKOL Decaglyn 3-OV), decaglyceryl pentaoleate (NIKKOL Decaglyn 5-OV) and tetraglyceryl monooleate (NIKKOL Tetraglyn 1-OV), with glyceryl monooleate, decaglyceryl monooleate and glyceryl monostearate, among others decaglyceryl monooleate, being preferred. These may be used alone or in combination of two or more. The term "glycerin fatty acid ester" as used in the present invention means all of such compounds.

Content of the glycerin fatty acid ester in the self-emulsifying composition of the present invention is not particularly limited as long as the merits of the present invention are not adversely affected. The content is generally 1 to 25% by weight, preferably 3 to 20% by weight, more preferably 5 to 15% by weight, and even more preferably 6 to 10% by weight when the self-emulsifying composition is defined to be 100% by weight as a whole, or 1 to 20% by weight, preferably 1 to 15% by weight, more preferably 1 to 10% by weight, and even more preferably 1 to 8% by weight when the self-emulsifying composition is defined to be 100% by weight as a whole.

In the present invention, the "polyoxyethylene castor oil" is a compound prepared by addition polymerization of ethylene oxide to castor oil. Various compounds with different average degrees of polymerization of ethylene oxide are commercially available, and examples include NIKKOL CO-3 (Nikko Chemicals Co., Ltd.) with an average ethylene oxide mole number of 3, NIKKOL CO-10 (Nikko Chemicals Co., Ltd.) with an average ethylene oxide mole number of 10, EMALEX C-20 (Nippon Emulsion Co., Ltd.) with an average ethylene oxide mole number of 20, EMALEX C-30 (Nippon Emulsion Co., Ltd.) with an average ethylene oxide mole number of 30, Kolliphor EL (BASF) (polyoxyl 35 castor oil) with an average ethylene oxide mole number of 35, EMALEX C-40 (Nippon Emulsion Co., Ltd.) with an average ethylene oxide mole number of 40, and EMALEX C-50 (Nippon Emulsion Co., Ltd.) with an average ethylene oxide mole number of 50, and the preferred is Kolliphor EL. These may be used alone or in combination of two or more. The term "polyoxyethylene castor oil" as used in the present invention means all of such compounds unless otherwise noted.

Content of the polyoxyethylene castor oil in the self-emulsifying composition of the present invention is not particularly limited as long as the merits of the present invention are not adversely affected. The content is generally 1 to 20% by weight, preferably 2 to 15% by weight, more preferably 3 to 10% by weight, and even more preferably 4 to 6% by weight when the self-emulsifying composition is defined to be 100% by weight as a whole.

Preferred embodiments of the self-emulsifying composition of the invention are as described in the following i) and/or ii).

i) A preferred embodiment of the inventive self-emulsifying composition contains at least a polyoxyethylene sorbitan fatty acid ester as an emulsifier. More preferably, the inventive composition contains a polyoxyethylene sorbitan fatty acid ester as a chief emulsifier. In another preferred embodiment, the emulsifying agent to be used for the composition is essentially composed of a polyoxyethylene sorbitan fatty acid ester and at least one selected from among a sorbitan fatty acid ester, a glycerin fatty acid ester and a polyoxyethylene castor oil.

The amount of a polyoxyethylene sorbitan fatty acid ester contained as a chief emulsifier will be at least 40 parts by weight, preferably at least 50 parts by weight, and more preferably at least 60 parts by weight when the total amount of emulsifiers contained in the composition is defined as 100 parts by weight. The amount of at least one emulsifier selected from among a sorbitan fatty acid ester, a glycerin fatty acid ester and a polyoxyethylene castor oil and used in combination with the polyoxyethylene sorbitan fatty acid ester will be up to 60 parts by weight, preferably up to 50 parts by weight, and more preferably up to 40 parts by weight when the total amount of the emulsifying agent to be used for the composition is defined as 100 parts by weight.

ii) Still another preferred embodiment of the inventive self-emulsifying composition contains at least two selected from among a sorbitan fatty acid ester, a glycerin fatty acid ester and a polyoxyethylene castor oil. This embodiment may not contain a polyoxyethylene sorbitan fatty acid ester.

While the combination of two emulsifiers is not particularly limited, preferred are combinations of a sorbitan fatty acid ester and a polyoxyethylene castor oil, of a glycerin fatty acid ester and a polyoxyethylene castor oil, and of a sorbitan fatty acid ester and a glycerin fatty acid ester, with a combination of a sorbitan fatty acid ester and a polyoxyethylene castor oil and a combination of a glycerin fatty acid ester and a polyoxyethylene castor oil being more preferred.

In this embodiment, the amount of an emulsifier contained in the composition in a larger amount than any other emulsifier is preferably up to 75 parts by weight, more preferably up to 67 parts by weight, and even more preferably up to 60 parts by weight when the total amount of emulsifiers contained in the composition is defined as 100 parts by weight. In some cases, the amount of such emulsifier is preferably 30 to 80 parts by weight, more preferably 35 to 70 parts by weight, even more preferably 38 to 67 parts by weight, and most preferably 40 to 55 parts by weight.

In the self-emulsifying composition of the present invention, a plurality of emulsifiers including a polyoxyethylene castor oil may be used as an emulsifying agent. The amount of polyoxyethylene castor oil contained in the composition is preferably up to 70 parts by weight, more preferably up to 60 parts by weight, and even more preferably up to 50 parts by weight when the total amount of emulsifiers contained in the composition is defined as 100 parts by weight. In some cases, the amount of polyoxyethylene castor oil is preferably 10 to 70 parts by weight, more preferably 15 to 60 parts by weight, even more preferably 17 to 40 parts by weight, and most preferably 18 to 30 parts by weight.

The self-emulsifying composition of the present invention may also contain an emulsifier other than the polyoxyethylene sorbitan fatty acid ester, sorbitan fatty acid ester, glycerin fatty acid ester and polyoxyethylene castor oil, while the amount of such an emulsifier is up to 20 parts by weight, preferably up to 10 parts by weight, more preferably up to 5 parts by weight, and most preferably none when the total amount of emulsifiers used for the composition is defined as 100 parts by weight. The additional emulsifier is not particularly limited as long as it satisfies at least one of the demands as described above, and exemplary additional emulsifiers include polyoxyethylene hydrogenated castor oil, propylene glycol fatty acid ester, saturated polyglycolated glyceride, polyoxyethylene polypropylene glycol, and sucrose fatty acid ester.

The total content of emulsifiers in the self-emulsifying composition of the present invention is not particularly limited as long as the merits of the present invention are not adversely affected. The total emulsifier content is generally 1 to 29% by weight, preferably 5 to 29% by weight, more preferably 6 to 29% by weight, still more preferably 7 to 29% by weight, and even more preferably 8 to 29% by weight, especially 9 to 29% by weight, when the self-emulsifying composition is defined to be 100% by weight as a whole. In some cases, the total emulsifier content is preferably 5 to 24% by weight, and more preferably 10 to 20% by weight. In alternative cases, the total emulsifier content is preferably 6 to 28% by weight, more preferably 8 to 26% by weight, and even more preferably 9 to 25% by weight. In addition, the total amount of emulsifiers contained in the composition is 5 to 45 parts by weight, preferably 10 to 45 parts by weight, more preferably 15 to 35 parts by weight, and even more preferably 15 to 20 parts by weight in relation to 100 parts by weight of the ω3 PUFA.

The composition and the pharmaceutical preparation of the present invention contain a small amount of water. Addition of water to a composition containing a hydrophobic lipid is generally conceived as a loss of compatibility. Presence of a specified amount of water in the inventive composition results in an improved compatibility of the composition, makes the use of a polyhydric alcohol and ethanol unnecessary, and thus allows the product which has a transparent appearance and gets rid of the problem of separation or cloudiness of a composition, even though not containing a polyhydric alcohol, ethanol or lecithin.

A small amount of water may be added during the preparation of the self-emulsifying composition, or the water in the gelatin capsule film may transfer to the self-emulsifying composition after the encapsulation of the self-emulsifying composition in the capsule.

In addition, the composition free from the polyhydric alcohol and the ethanol does not cause the capsule to be softened or deformed after the encapsulation, nor has side effects of the ethanol on alcohol intolerance patients taking the composition.

The water content of the self-emulsifying composition is preferably 0.5 to 6% by weight, more preferably 0.5 to 4% by weight, still more preferably 0.5 to 3% by weight, and even more preferably 0.5 to 2.5% by weight, with a content of 0.7 to 1.5% by weight being most preferred, when the composition is defined to be 100% by weight as a whole.

The water content is preferably 1 to 30% by weight, more preferably 2 to 25% by weight, still more preferably 3 to 20% by weight, and even more preferably 4 to 15% by weight, with a content of 5 to 9% by weight being most preferred, when the total amount of emulsifiers contained in the self-emulsifying composition is defined as 100 parts by weight.

In the present invention, the "lecithin" is a type of glycerophospholipid, and examples include soybean lecithin, zymolytic soybean lecithin, hydrogenated soybean lecithin, egg yolk lecithin, hydrogenated phospholipid, phospholipid from milk, lysolecithin, phosphatidyl choline, and phosphatidyl serine. The preferred are soybean lecithin, zymolytic soybean lecithin, hydrogenated soybean lecithin, and egg yolk lecithin, and the more preferred is soybean lecithin. These may be used alone or in combination of two or more. The term "lecithin" as used in the present invention means all of such glycerophospholipids unless otherwise noted. In the present invention, lecithin is not included in the emulsifying agent.

Various lecithins are commercially available, and exemplary such products include purified soybean lecithin (Nisshin Oilio), purified egg yolk lecithin (Asahi Kasei Pharma Corporation), and egg yolk lecithin PL-100M (Kewpie Corporation), and use of such products is also possible. Exemplary soybean lecithins include BASIS LP-20B (Nisshin Oil Mills, Ltd.) and Lipoid S45 and S20 (Lipoid), and exemplary zymolytic lecithins include BASIS LP-20E (Nisshin Oil Mills, Ltd.) and Phospholipon RLPC20 (Lipoid). Various such commercially available products may be used in the composition.

In a preferred embodiment of the self-emulsifying composition of the present invention, essentially no lecithin is contained. For instance, 3 or more parts by weight of lecithin is not contained in the composition in relation to 100 parts by weight of the ω3 PUFA. In other words, the amount of lecithin contained in the composition is less than 3 parts by weight, preferably less than 2 parts by weight, more preferably less than 1 part by weight, and most preferably 0 parts by weight. The amount of lecithin contained in the inventive self-emulsifying composition is preferably 0 parts by weight or more but less than 3 parts by weight, and more preferably 0 parts by weight or more but less than 1 part by weight.

The lecithin content is preferably lower than 2.1% by weight, more preferably lower than 1.4% by weight, and even more preferably lower than 0.7% by weight when the self-emulsifying composition is defined to be 100% by weight as a whole.

In the present invention, the "polyhydric alcohol" is a polyol compound having the structure of a straight chain or cyclic aliphatic hydrocarbon wherein two or more carbon atoms are each substituted with one hydroxy group. Exemplary such polyhydric alcohols include divalent alcohols such as ethylene glycol, propylene glycol, ethylene glycol, 1,2-butylene glycol, tetramethylene glycol, 1,3-butylene glycol, 2,3-butylene glycol, and pentamethylene glycol; trivalent alcohols such as glycerin, trimethylolpropane, and 1,2,6-hexane triol; and polyhydric alcohol polymers such as diethylene glycol, dipropylene glycol triethylene glycol, polyethylene glycol, polypropylene glycol, and polyglycerin, and the preferred is propylene glycol or glycerin. The glycerin also includes concentrated glycerin. The term "polyhydric alcohol" as used in the present invention means all of such polyol compounds unless otherwise noted.

Advantageously, the content of the polyhydric alcohol in the self-emulsifying composition of the present invention is such that it does not cause a capsule filled with the composition to be deformed. In a preferred embodiment, the inventive composition contains essentially no polyhydric alcohol. In other words, the composition does not contain the polyhydric alcohol at a content higher than 4% by weight, for instance, when the composition is defined to be 100% by weight as a whole. Alternatively, the polyhydric alcohol content is up to 4% by weight, preferably up to 3% by weight, more preferably up to 2% by weight, even more preferably up to 1% by weight, and most preferably 0% by weight.

Advantageously, the content of the ethanol in the self-emulsifying composition of the present invention is such that change in the quality is not induced during the encapsulation, distribution or storage, and denaturing of the capsule content is not induced either, and the ethanol content should not exceed the daily experientially allowable medical dose. In a preferred embodiment, the inventive composition contains essentially no ethanol. In other words, the composition does not contain the ethanol at a content higher than 4% by weight, for instance, when the composition is defined to be 100% by weight as a whole. Alternatively, the ethanol content is up to 4% by weight, preferably up to 3% by weight, more preferably up to 2% by weight, even more preferably up to 1% by weight, and most preferably 0% by weight.

When the ethanol and the polyhydric alcohol are added in the composition, the total content of the ethanol and the polyhydric alcohol is preferably not more than 4% by weight when the composition is defined to be 100% by weight as a whole. The total content of the ethanol and the polyhydric alcohol in the composition is preferably up to 4% by weight, more preferably up to 3% by weight, still more preferably up to 2% by weight, even more preferably up to 1% by weight, and most preferably 0% by weight.

Preferable ethanol concentration may be determined based on the ω3 PUFA concentration of the self-emulsifying composition and the daily dose of the self-emulsifying composition. When the self-emulsifying composition of the present invention is orally administered at a daily dose of 1800 mg in terms of ω3 PUFA, and a preparation containing the ω3 PUFA, for example, at 75% by weight is prepared, the ethanol dose will not exceed 3.26 mg which is daily maximum dose described in the "Dictionary of Pharmaceutical Additives" when the ethanol concentration is up to 0.135% by weight.

For the self-emulsifying composition of the present invention containing such ω3 PUFA and emulsifying agent as described above, a preferred embodiment is the combination containing 1) EPA-E and/or DHA-E, 2) water, and 3) a polyoxyethylene sorbitan fatty acid ester as an emulsifier. Another preferred embodiment is the combination of 1) EPA-E and/or DHA-E, 2) water, and 3) at least two emulsifiers selected from the group consisting of a sorbitan fatty acid ester, a glycerin fatty acid ester and a polyoxyethylene castor oil.

Another preferred embodiment is the combination of 1) EPA-E and/or DHA-E, 2) water, 3) a polyoxyethylene sorbitan fatty acid ester as an emulsifier, and 4) at least one emulsifier selected from the group consisting of a sorbitan fatty acid ester, a glycerin fatty acid ester and a polyoxyethylene castor oil. Yet another preferred embodiment is the combination of 1) EPA-E and/or DHA-E, 2) water, 3) a polyoxyethylene sorbitan fatty acid ester as an emulsifier, and 4) at least two emulsifiers selected from the group consisting of a sorbitan fatty acid ester, a glycerin fatty acid ester and a polyoxyethylene castor oil.

In each of such self-emulsifying compositions, the content of the EPA-E and/or DHA-E 1) is 70 to 90% by weight, the content of the water 2) is 0.5 to 6% by weight, and the content of the emulsifier or emulsifiers 3) is 1 to 29% by weight when the relevant composition is defined to be 100% by weight as a whole.

The self-emulsifying composition of the present invention may be encapsulated in a capsule. The capsule selected may be a hard capsule or a soft capsule, and preferably, the capsule used is a soft capsule. The soft capsule is not particularly limited in shape, and preferably, the soft capsule is a rotary die type soft capsule or a seamless capsule.

In the soft capsule of the present invention, the capsule film is not necessarily limited for its composition, and exemplary main ingredients include gelatin, carageenan, pectin, pullulan, sodium arginate, starch, hypromellose, hydroxypropyl cellulose, and other known ingredients. The preferred is gelatin, and the type of gelatin used is not particularly limited. Exemplary gelatins include acid-treated gelatin, alkali-treated gelatin, amphoteric gelatin, chemically modified gelatin, and other known gelatins, which may be used alone or in combination of two or more. The gelatin used is preferably an acid-treated gelatin or alkali-treated gelatin. The source of the gelatin is not necessarily limited, and the gelatin used may be the one from cattle bone, cattle skin, pig bone, pig skin, fish scale, or fish skin, and preferably, the one from cattle bone, cattle skin, pig bone, or pig skin.

The "gelatin" used may be the one normally used in the production of a soft capsule, for example, medical gelatin (gelatin and purified gelatin) defined in The Japanese Pharmacopoeia 16th edition. The gelatin may also be a combination of two or more types, and the capsule film may also contain other components such as a plasticizing agent.

The "plasticizing agent" added to the capsule film may be the one normally used in the production of a soft capsule, with preferred examples including a polyhydric alcohol such as glycerin (for example, concentrated glycerin), ethylene glycol, polyethylene glycol, propylene glycol, or polypropylene glycol, and a sugar alcohol such as sorbitol, mannitol, or xylitol. These plasticizing agents may be used in combination of two or more. Particularly preferred are glycerin and sorbitol. Also preferred is a combination of glycerin and sorbitol, and in this case, the glycerin and the sorbitol may be used at a weight ratio in the range of 1:5 to 5:1, and more preferably 1:3 to 3:1.

In the soft capsule preparation, and in particular, in the seamless capsule of the present invention, the capsule film solution preferably contains the gelatin and the plasticizing agent at a weight ratio in the range of 10:1 to 1:10, and more preferably of 10:1 to 1:1.

The weight ratio between the capsule film solution and the capsule content is typically 10:1 to 1:10, and preferably 3:1 to 1:10.

If desired, the capsule film may also contain various additives commonly used in the capsule film. Exemplary such additives include amino acids, citric acid, glycerin, sorbitol, trehalose, and other plasticizing agents, antiseptic, dye, titanium oxide, and other colorants, and organic acids.

The composition for the capsule film may be prepared by dissolving gelatin, the plasticizing agent, and the optional additives in water at room temperature or at an elevated temperature.

A capsulated self-emulsifying preparation having the self-emulsifying composition of the present invention as its liquid content preferably has high hardness immediately after the production, and this hardness is preferably maintained during the storage. Loss of the hardness is unfavorable in view of the quality because the loss of the hardness does not only result in the deformation but also fragileness and breakage of the capsule and bleeding of the content. Softening of the capsule can be detected by measuring the hardness with a common hardness tester.

The capsulated self-emulsifying preparation of the present invention has the hardness immediately after the production of at least 18 kgf, preferably at least 20 kgf, and more preferably at least 22 kgf. It is desirable that the hardness of the preparation does not substantially decrease, or not decrease by 6 kgf or more when the preparation is stored in a tightly sealed aluminum package at 40° C. for 1 week compared with the hardness immediately after the production. Preferably, the inventive preparation has a hardness of at least 10 kgf, more preferably of at least 15 kgf, and even more preferably of at least 20 kgf after the storage at 40° C. for 1 week.

With the hardness immediately after the production being assumed to be 100%, at least 60%, preferably at least 70%, more preferably at least 80%, and most preferably at least 90% thereof is exhibited (maintained) after the storage in a tightly sealed aluminum package at 40° C. for 1 week.

The dose and dosage period of the ω3 PUFA used in the self-emulsifying composition of the present invention are made sufficient for realizing the intended action, and can be adequately adjusted depending on the administration route, frequency of administration per day, seriousness of the symptoms, body weight, age, and other factors.

In the case of oral administration, the composition is administered one to three times a day at an EPA-E dose, for instance, of 0.1 to 5 g/day, preferably of 0.2 to 3 g/day, more preferably of 0.3 to 3 g/day, still more preferably of 0.5 to 3 g/day, and even more preferably of 0.9 to 3 g/day. The administration may be conducted one time at the entire dose or several times at divided doses as required. The frequency of administration per day is preferably one time a day or two or three times a day. In the case of one time administration per day, one to ten capsules, preferably one to eight capsules, more preferably one to six capsules, still more preferably one to four capsules, and even more preferably one to three capsules as soft capsules each containing 1 g of EPA-E, for instance, can be administered. Soft capsules each containing 1 g of EPA-E may be combined with soft capsules each containing 0.5 g of the ester so as to administer the composition at an EPA-E dose of 0.5 g, 1.5 g, 2.5 g, 3.5 g, 4.5 g or 5.5 g/administration.

While administration of EPA-E during to after meals is deemed preferable, and administration immediately after meals (within 30 minutes after meals) more preferable, because the absorption of EPA-E is influenced by diet, the self-emulsifying composition of the present invention has an excellent absorbability under fasting, and therefore, it exerts the intended effects even when administered at a timing other than during, after or immediately after meals, for example, before or immediately before meals, between meals, or at bedtime; when administered to patients with reduced absorption ability of the intestinal tract (for example, elderly, patients of intestinal disease, patients after intestinal surgery, terminal cancer patients, or patients taking a lipase inhibitor); or when administered at a reduced dose.

The self-emulsifying composition of the present invention is preferably characterized in that the time until the maximum blood concentration is attained after the oral administration is comparable to or shorter than that found for the ω3 PUFA stock solution. Otherwise, the inventive composition is preferably characterized in that the maximum blood concentration is higher than that found for the ω3 PUFA stock solution. In addition, the inventive composition is preferably characterized in that the blood concentration two hours after the administration, the area under the blood concentration vs time curve from zero to two hours after the administration, and/or the area under the blood concentration vs time curve from zero to 72 hours after the administration is comparable to or higher than that found for the ω3 PUFA stock solution. More preferably, the self-emulsifying composition of the present invention is characterized in that the time until the maximum blood concentration is attained is short, the maximum blood concentration is high, and both the blood concentration two hours after the administration and the area under the blood concentration vs time curve from zero to two hours and/or from zero to 72 hours after the administration are high as compared with those for the ω3 PUFA stock solution, respectively.

Such pharmacokinetics as above can be confirmed with dogs, monkeys or other animals, and preferably by examination on humans.

In a pharmacokinetic study conducted by orally administering the self-emulsifying composition to male beagles as fasted for at least 18 hours at an ω3 PUFA dose of 600 mg, the maximum ω3 PUFA blood concentration is, for instance, preferably at least 50 µg/mL, more preferably at least 60 µg/mL, and even more preferably at least 70 µg/mL, as calculated with correction by subtraction of the blood ω3 polyunsaturated fatty acid concentration before the administration of the composition. The area under the blood ω3 PUFA concentration vs time curve from zero to two hours after the administration is preferably at least 50 µg/mL·hr, more preferably at least 60 µg/mL·hr, and even more preferably at least 70 µg/mL·hr. The combination of the ranges of the maximum ω3 PUFA blood concentration and the area under the blood ω3 PUFA concentration vs time curve is preferably a combination of the range of at least 50 µg/mL and the range of at least 50 µg/mL·hr, more preferably a combination of the range of at least 60 µg/mL and the range of at least 60 µg/mL·hr, and even more preferably a combination of the range of at least 70 µg/mL and the range of at least 70 µg/mL·hr.

In a pharmacokinetic study conducted by orally administering the self-emulsifying composition to male crab-eating macaques as fasted for at least 12 hours at an ω3 dose of 45 mg/kg body weight, the maximum ω3 PUFA blood concentration is preferably at least 50 µg/mL, and more preferably at least 70 µg/mL, as calculated with correction by subtraction of the blood ω3 polyunsaturated fatty acid concentration before the administration of the composition. The area under the blood ω3 PUFA concentration vs time curve from zero to 12 hours after the administration is preferably at least 400 µg/mL·hr, and more preferably at least 500 µg/mL. The combination of the ranges of the maximum ω3 PUFA blood concentration and the area under the blood ω3 PUFA concentration vs time curve as above is preferably a combination of the range of at least 50 µg/mL and the range of at least 400 µg/mL·hr, and more preferably a combination of the range of at least 70 µg/mL and the range of at least 500 µg/mL·hr.

In a pharmacokinetic study conducted by orally administering the self-emulsifying composition to humans at such a timing as before meals, immediately after meals or after meals at an ω3 PUFA or EPA dose of 1800 mg, the maximum ω3 PUFA blood concentration is preferably at least 50 µg/mL, more preferably at least 100 µg/mL, still more preferably at least 150 µg/mL, even more preferably at least 200 µg/mL, and most preferably at least 300 µg/mL, as calculated with correction by subtraction of the blood ω3 polyunsaturated fatty acid concentration before the administration of the composition. Alternatively, the maximum ω3 PUFA blood concentration is preferably 10 to 1000 µg/mL, more preferably 20 to 500 µg/mL, still more preferably 40 to 300 µg/mL, even more preferably 50 to 150 µg/mL, and most preferably 50 to 100 µg/mL. The area under the blood ω3 PUFA concentration vs time curve from zero to 72 hours after the administration is preferably at least 500 µg/mL·hr, more preferably at least 1000 µg/mL·hr, still more preferably at least 1500 µg/mL·hr, even more preferably at least 2000 µg/mL·hr, and most preferably at least 3000 µg/mL·hr. Alternatively, the area under the blood ω3 PUFA concentration vs time curve as above is preferably 500 to 4500 µg/mL·hr, more preferably 600 to 3000 µg/mL·hr, still more preferably 700 to 2500 µg/mL·hr, even more preferably 800 to 2000 µg/mL·hr, and most preferably 1000 to 1500 µg/mL·hr. The time until the maximum plasma concentration is attained is preferably up to 6 hours, more preferably up to 5 hours, still more preferably up to 3 hours, even more preferably up to 1 hour, and most preferably less than one hour. Alternatively, the time until the maximum plasma concentration is attained is preferably 0.5 to 10 hours, more preferably 1 to 8 hours, still more preferably 1.5 to 7 hours, even more preferably 2 to 5 hours, and most preferably 2.5 to 4 hours. The plasma elimination half-life is preferably at least 10 hours, more preferably at least 20 hours, still more preferably at least 30 hours, even more preferably at least 40 hours, and most preferably at least 50 hours. Alternatively, the plasma elimination half-life is preferably 0 to 150 hours, more preferably 10 to 120 hours, still more preferably 30 to 100 hours, even more preferably 25 to 75 hours, and most preferably 25 to 50 hours.

In a pharmacokinetic study conducted by orally administering the self-emulsifying composition to humans at such a timing as before meals, immediately after meals or after meals at an ω3 PUFA or EPA dose of 3600 mg, the maximum ω3 PUFA blood concentration is preferably at least 50 µg/mL, more preferably at least 100 µg/mL, still more preferably at least 150 µg/mL, even more preferably at least 200 µg/mL, and most preferably at least 300 µg/mL, as calculated with correction by subtraction of the blood ω3 polyunsaturated fatty acid concentration before the administration of the composition. Alternatively, the maximum ω3 PUFA blood concentration is preferably 10 to 1000 µg/mL, more preferably 20 to 500 µg/mL, still more preferably 50 to 400 µg/mL, even more preferably 100 to 300 µg/mL, and most preferably 150 to 200 µg/mL. The area under the blood ω3 PUFA concentration vs time curve from zero to 72 hours after the administration is preferably at least 500 µg/mL·hr, more preferably at least 1000 µg/mL·hr, still more preferably at least 1500 µg/mL·hr, even more preferably at least 2000 µg/mL·hr, and most preferably at least 3000 µg/mL·hr. Alternatively, the area under the blood ω3 PUFA concentration vs time curve as above is preferably 500 to 5000 µg/mL·hr, more preferably 1000 to 4700 µg/mL·hr, still more preferably 1500 to 4500 µg/mL·hr, even more preferably 2000 to 4000 µg/mL·hr, and most preferably 2500 to 3500 µg/mL·hr. The time until the maximum plasma concentration is attained is preferably up to 6 hours, more preferably up to 5 hours, still more preferably up to 3 hours, even more preferably up to 1 hour, and most preferably less than one hour. Alternatively, the time until the maximum plasma concentration is attained is preferably 0.5 to 10 hours, more preferably 1 to 8 hours, still more preferably 1.5 to 7 hours, even more preferably 2 to 6 hours, and most preferably 3 to 5 hours. The plasma elimination half-life is preferably at least 10 hours, more preferably at least 20 hours, still more preferably at least 30 hours, even more preferably at least 40 hours, and most preferably at least 50 hours. Alternatively, the plasma elimination half-life is preferably 0 to 150 hours, more preferably 10 to 120 hours, still more preferably 30 to 100 hours, even more preferably 25 to 75 hours, and most preferably 25 to 50 hours.

In the case of a pharmacokinetic study with humans, the above-mentioned numerical ranges may also be replaced by those mentioned below. To be more specific: In a study conducted by orally administering the self-emulsifying composition at such a timing as before, immediately after or after meals at an EPA dose of 1800 mg, the maximum ω3 PUFA plasma concentration as calculated with correction by subtraction of the blood ω3 polyunsaturated fatty acid concentration before the administration of the composition is not particularly limited, while it may be specified to be: 10 to 50; 50 to 100; 100 to 150; 150 to 200; 200 to 250; 250 to 300; 300 to 350; 350 to 400; 400 to 450; 450 to 500; 500 to 600; 600 to 700; 700 to 800; 800 to 900; 900 to 1000; 10 to 30; 20 to 40; 30 to 50; 40 to 60; 50 to 70; 60 to 80; 70 to 90; 80 to 100; 90 to 110; 100 to 120; 110 to 130; 120 to 140; 130 to 150; 140 to 160; 150 to 170; 160 to 180; 170 to 190; 180 to 200; 190 to 210; 200 to 220; 220 to 240; 240 to 260; 260 to 280; 280 to 300; 10 to 20; 15 to 25; 20 to 30; 25 to 35; 30 to 40; 35 to 45; 40 to 50; 45 to 55; 50 to 55; 53 to 58; 55 to 60; 58 to 63; 60 to 65; 63 to 68; 65 to 70; 68 to 73; 70 to 75; 73 to 78; 75 to 80; 78 to 83; 80 to 85; 83 to 88; 85 to 90; 88 to 93; 90 to 95; 93 to 98; 95 to 100; 98 to 103; 100 to 105; 103 to 108; 105 to 110; 108 to 113; 110 to 115; 113 to 118; 115 to 120; 118 to 123; 120 to 125; 123 to 128; 125 to 130; 128 to 133; 130 to 135; 133 to 138; 135 to 140; 138 to 143; 140 to 145; 143 to 148; 145 to 150; 150 to 160; 155 to 165; 160 to 170; 165 to 175; 170 to 180; 175 to 185; 180 to 190; 185 to 195; 190 to 200; 195 to 205; 200 to 210; 205 to 215; 210 to 220; 215 to 225; 220 to 230; 225 to 235; 230 to 240; 235 to 245; or 240 to 250 µg/mL. In a study conducted by administering the self-emulsifying composition at such a timing as before, immediately after or after meals at an EPA dose of 3600 mg, the maximum ω3 PUFA plasma concentration may be specified to be: 10 to 50; 50 to 100; 100 to 150; 150 to 200; 200 to 250; 250 to 300; 300 to 350; 350 to 400; 400 to 450; 450 to 500; 500 to 600; 600 to 700; 700 to 800; 800 to 900; 900 to 1000; 10 to 30; 20 to 40; 30 to 50; 40 to 60; 50 to 70; 60 to 80; 70 to 90; 80 to 100; 90 to 110; 100 to 120; 110 to 130; 120 to 140; 130 to 150; 140 to 160; 150 to 170; 160 to 180; 170 to 190; 180 to 200; 190 to 210; 200 to 220; 220 to 240; 240 to 260; 260 to 280; 280 to 300; 10 to 20; 15 to 25; 20 to 30; 25 to 35; 30 to 40; 35 to 45; 40 to 50; 45 to 55; 50 to 55; 53 to 58; 55 to 60; 58 to 63; 60 to 65; 63 to 68; 65 to 70; 68 to 73; 70 to 75; 73 to 78; 75 to 80; 78 to 83; 80 to 85; 83 to 88; 85 to 90; 88 to 93; 90 to 95; 93 to 98; 95 to 100; 98 to 103; 100 to 105; 103 to 108; 105 to 110; 108 to 113; 110 to 115; 113 to 118; 115 to 120; 118 to 123; 120 to 125; 123 to 128; 125 to 130; 128 to 133; 130 to 135; 133 to 138; 135 to 140; 138 to 143; 140 to 145; 143 to 148; 145 to 150; 150 to 160; 155 to 165; 160 to 170; 165 to 175; 170 to 180; 175 to 185; 180 to 190; 185 to 195; 190 to 200; 195 to 205; 200 to 210; 205 to 215; 210 to 220; 215 to 225; 220 to 230; 225 to 235; 230 to 240; 235 to 245; or 240 to 250 µg/mL.

The area under the blood ω3 PUFA concentration vs time curve from zero to 72 hours after the administration in a study conducted by administering the self-emulsifying composition at such a timing as before, immediately after or after meals at an EPA dose of 1800 mg may be specified to be: 500 to 1500; 1000 to 2000; 1500 to 2500; 2000 to 3000; 2500 to 3500; 3000 to 4000; 500 to 1000; 750 to 1250; 1000 to 1500; 1250 to 1750; 1500 to 2000; 1750 to 2250; 2000 to 2500; 2250 to 2750; 2500 to 3000; 2750 to 3250; 3000 to 3500; 3250 to 3750; 3500 to 4000; 3750 to 4250; 4000 to 4500; 4250 to 4750; 4500 to 5000; 500 to 700; 600 to 800; 700 to 900; 800 to 1000; 900 to 1100; 1000 to 1200; 1100 to 1300; 1200 to 1400; 1300 to 1500; 1400 to 1600; 1500 to 1700;

1600 to 1800; 1700 to 1900; 1800 to 2000; 1900 to 2100; 2000 to 2200; 2100 to 2300; 2200 to 2400; 2300 to 2500; 2400 to 2600; 2500 to 2700; 2600 to 2800; 2700 to 2900; 2800 to 3000; 2900 to 3100; 3000 to 3200; 3100 to 3300; 3200 to 3400; 3300 to 3500; 3400 to 3600; 3500 to 3700; 3600 to 3800; 3700 to 3900; 3800 to 4000; 3900 to 4100; 4000 to 4200; 4100 to 4300; 4200 to 4400; 4300 to 4500; 500 to 600; 550 to 650; 600 to 700; 650 to 750; 700 to 800; 750 to 850; 800 to 900; 850 to 950; 900 to 1000; 950 to 1050; 1000 to 1100; 1050 to 1150; 1100 to 1200; 1150 to 1250; 1200 to 1300; 1250 to 1350; 1300 to 1400; 1350 to 1450; 1400 to 1500; 1450 to 1550; 1500 to 1600; 1550 to 1650; 1600 to 1700; 1650 to 1750; 1700 to 1800; 1750 to 1850; 1800 to 1900; 1850 to 1950; 1900 to 2000; 1950 to 2050; 2000 to 2100; 2050 to 2150; 2100 to 2200; 2150 to 2250; 2200 to 2300; 2250 to 2350; 2300 to 2400; 2350 to 2450; 2400 to 2500; 2450 to 2550; 2500 to 2600; 2550 to 2650; 2600 to 2700; 2650 to 2750; 2700 to 2800; 2750 to 2850; 2800 to 2900; 2850 to 2950; 2900 to 3000; 2950 to 3050; 3000 to 3100; 3150 to 3250; 3200 to 3300; 3250 to 3350; 3300 to 3400; 3350 to 3450; 3400 to 3500; 3500 to 3600; 3600 to 3700; 3700 to 3800; 3800 to 3900; 3900 to 4000; 4000 to 4100; 4100 to 4200; 4200 to 4300; 4300 to 4400; or 4400 to 4500 µg/mL·hr. In a study conducted by administering the self-emulsifying composition at such a timing as before, immediately after or after meals at an EPA dose of 3600 mg, the area under the blood ω3 PUFA concentration vs time curve as above may be specified to be: 500 to 1500; 1000 to 2000; 1500 to 2500; 2000 to 3000; 2500 to 3500; 3000 to 4000; 500 to 1000; 750 to 1250; 1000 to 1500; 1250 to 1750; 1500 to 2000; 1750 to 2250; 2000 to 2500; 2250 to 2750; 2500 to 3000; 2750 to 3250; 3000 to 3500; 3250 to 3750; 3500 to 4000; 3750 to 4250; 4000 to 4500; 4250 to 4750; 4500 to 5000; 500 to 700; 600 to 800; 700 to 900; 800 to 1000; 900 to 1100; 1000 to 1200; 1100 to 1300; 1200 to 1400; 1300 to 1500; 1400 to 1600; 1500 to 1700; 1600 to 1800; 1700 to 1900; 1800 to 2000; 1900 to 2100; 2000 to 2200; 2100 to 2300; 2200 to 2400; 2300 to 2500; 2400 to 2600; 2500 to 2700; 2600 to 2800; 2700 to 2900; 2800 to 3000; 2900 to 3100; 3000 to 3200; 3100 to 3300; 3200 to 3400; 3300 to 3500; 3400 to 3600; 3500 to 3700; 3600 to 3800; 3700 to 3900; 3800 to 4000; 3900 to 4100; 4000 to 4200; 4100 to 4300; 4200 to 4400; 4300 to 4500; 500 to 600; 550 to 650; 600 to 700; 650 to 750; 700 to 800; 750 to 850; 800 to 900; 850 to 950; 900 to 1000; 950 to 1050; 1000 to 1100; 1050 to 1150; 1100 to 1200; 1150 to 1250; 1200 to 1300; 1250 to 1350; 1300 to 1400; 1350 to 1450; 1400 to 1500; 1450 to 1550; 1500 to 1600; 1550 to 1650; 1600 to 1700; 1650 to 1750; 1700 to 1800; 1750 to 1850; 1800 to 1900; 1850 to 1950; 1900 to 2000; 1950 to 2050; 2000 to 2100; 2050 to 2150; 2100 to 2200; 2150 to 2250; 2200 to 2300; 2250 to 2350; 2300 to 2400; 2350 to 2450; 2400 to 2500; 2450 to 2550; 2500 to 2600; 2550 to 2650; 2600 to 2700; 2650 to 2750; 2700 to 2800; 2750 to 2850; 2800 to 2900; 2850 to 2950; 2900 to 3000; 2950 to 3050; 3000 to 3100; 3150 to 3250; 3200 to 3300; 3250 to 3350; 3300 to 3400; 3350 to 3450; 3400 to 3500; 3500 to 3600; 3600 to 3700; 3700 to 3800; 3800 to 3900; 3900 to 4000; 4000 to 4100; 4100 to 4200; 4200 to 4300; 4300 to 4400; or 4400 to 4500 µg/mL·hr.

The time until the maximum plasma concentration is attained in a study conducted by administering the self-emulsifying composition at such a timing as before, immediately after or after meals at an EPA dose of 1800 mg or 3600 mg may be specified to be: 0 to 2; 1 to 3; 2 to 4; 3 to 5; 4 to 6; 5 to 7; 6 to 8; 7 to 9; 8 to 10; 0 to 1; 0.5 to 1.5; 1 to 2; 1.5 to 2.5; 2 to 3; 2.5 to 3.5; 3 to 4; 3.5 to 4.5; 4 to 5; 4.5 to 5.5; 5 to 6; 5.5 to 6.5; 6 to 7; 6.5 to 7.5; 7 to 8; 7.5 to 8.5; 8 to 9; 8.5 to 9.5; 9 to 10; 0 to 0.5; 0.3 to 0.8; 0.5 to 1; 0.8 to 1.3; 1 to 1.5; 1.3 to 1.8; 1.5 to 2; 1.8 to 2.3; 2 to 2.5; 2.3 to 2.8; 2.5 to 3; 2.8 to 3.3; 3 to 3.5; 3.3 to 3.8; 3.5 to 4; 3.8 to 4.3; 4 to 4.5; 4.3 to 4.8; 4.5 to 5; 4.8 to 5.3; 5 to 5.5; 5.3 to 5.8; 5.5 to 6; 5.8 to 6.3; 6 to 6.5; 6.3 to 6.8; 6.5 to 7; 6.8 to 7.3; 7 to 7.5; 7.3 to 7.8; 7.5 to 8; 7.8 to 8.3; 8 to 8.5; 8.3 to 8.8; 8.5 to 9; 8.8 to 9.3; 9 to 9.5; 9.3 to 9.8; or 9.5 to 10 hours.

The plasma elimination half-life in a study conducted by administering the self-emulsifying composition at such a timing as before, immediately after or after meals at an EPA dose of 1800 mg or 3600 mg may be specified to be: 0 to 50; 25 to 75; 50 to 100; 75 to 125; 100 to 150; 125 to 175; 150 to 200; 0 to 20; 10 to 30; 20 to 40; 30 to 50; 40 to 60; 50 to 70; 60 to 80; 70 to 90; 80 to 100; 90 to 110; 100 to 120; 110 to 130; 120 to 140; 130 to 150; 0 to 10; 5 to 15; 10 to 20; 15 to 25; 20 to 30; 25 to 35; 30 to 40; 35 to 45; 40 to 50; 45 to 55; 50 to 60; 55 to 65; 60 to 70; 65 to 75; 70 to 80; 75 to 85; 80 to 90; 85 to 95; 90 to 100; 95 to 105; 100 to 110; 105 to 115; or 110 to 120 hours.

The present invention may be defined by a combination of two or more selected from among the maximum ω3 PUFA plasma concentration, the area under the blood ω3 PUFA concentration vs time curve from zero to 72 hours after the administration, the time until the maximum plasma concentration is attained, and the plasma elimination half-life.

The self-emulsifying composition of the present invention may also contain additives such as an emulsification aid, stabilizer, antiseptic, surfactant, and antioxidant. Exemplary emulsification aids include fatty acids containing 12 to 22 carbon atoms such as stearic acid, oleic acid, linoleic acid, palmitic acid, linolenic acid, and myristic acid and their salts. Exemplary stabilizers include phosphatidic acid, ascorbic acid, glycerin, and cetanols, and exemplary antiseptics include ethyl paraoxybenzoate and propyl paraoxybenzoate. Exemplary antioxidants include oil-soluble antioxidants such as butylated hydroxy toluene, butylated hydroxy anisole, propyl gallate, propyl gallate, pharmaceutically acceptable quinone, astaxanthin, and α-tocopherol.

In addition, an adequate carrier or vehicle, a colorant, a flavor, and optionally, a vegetable oil and an additive such as non-toxic organic solvent or non-toxic solubilizing agent, emulsifier, suspending agent (for example, Tween 80 and gum arabic solution), isotonic agent, pH adjusting agent, stabilizer, corrective, flavoring agent, preservative, antioxidant, or absorption promoter commonly used in the art may be adequately combined with the inventive composition to prepare an appropriate pharmaceutical preparation.

More specifically, since the ω3 PUFA is highly unsaturated, effective amount of an oil-soluble antioxidant, for example, at least one member selected from butylated hydroxytoluene, butylated hydroxyanisole, propyl gallate, propyl gallate, pharmaceutically acceptable quinone, astaxanthin, and α-tocopherol is preferably incorporated in the composition.

Since the self-emulsifying composition of the present invention is also used for pharmaceutical application, it preferably has good appearance, self-emulsifying property, composition dispersibility, emulsion stability, and storage stability. The appearance of the self-emulsifying composition is such that the composition is not separated, clouded, solidified, or precipitated, but transparent. The composition having poor appearance may be pharmaceutically unsuitable, and such composition may be insufficient in required performance such as self-emulsifying property.

With regard to the storage temperature, the self-emulsifying composition and the preparation prepared by encapsulating such composition is preferably transparent at both low temperature and high temperature in view of its use in cold district or hot environment.

In the case of the self-emulsifying composition having good self-emulsifying property, good dispersibility of the composition, and high emulsion stability, the composition rapidly disperses upon contact with water to form a micro-emulsion having adequate emulsion droplet diameter. Absorbability of an oil such as EPA-E is related to the size of the emulsion droplet diameter, and degree of the absorbability upon administration to the animal can be estimated by measuring the emulsion droplet diameter.

In the present invention, the "mean droplet diameter" is the value of volume mean diameter among droplets of the emulsified composition measured by using a particle size analyzer (for example, Nanotorac manufactured by Nikkiso Co., Ltd.) with water being used for the dispersion medium according to standard measurement method (for example, set zero time of 30 seconds, measurement time of 30 seconds, average of three measurements). The mean droplet diameter when the self-emulsifying composition of the present invention is dispersed in water or the like is not particularly limited as long as it is up to 2 μm, and the product has good emulsion dispersibility, good emulsion stability, or good absorbability, and the mean droplet diameter is typically up to 1.5 more preferably up to 1.0 μm, still more preferably up to 0.5 Jim, and most preferably up to 0.3 μm.

The self-emulsifying composition of the present invention may be used by combining with a second effective component. The second effective component may be any component adequately selected depending on the intended type and severity of the disease as long as it does not adversely affect the merits of the ω3 PUFAs. Exemplary such second effective components include therapeutic agents for hyperlipidemia, antihypertensives, antidiabetics, antioxidants, blood flow improving agents, bile acid derivatives, therapeutic agents for NAFLD and NASH, as well as progression suppressants and therapeutic agents for cognitive impairment.

Examples of a favorable second effective component include such therapeutic agents for hyperlipidemia as polyene phosphatidyl choline, unsaponifiable matter in soybean oil (soysterol), gamma orizanol, riboflavin butyrate, dextran sulfate sodium sulfur 18, pantethine, and elastase. Also included are statins such as pravastatin, simbastatin, atorvastatin, fluvastatin, pitavastatin, rosuvastatin and cerivastatin; fibrates such as simfibrate, clofibrate, clinofibrate, bezafibrate and fenofibrate; lipolytic enzyme inhibitors such as orlistat and cetilistat; resins such as cholestyramine and cholestyramide; and ezetimibe.

Exemplary antihypertensives include: angiotensin II receptor antagonists such as irbesartan, olmesartan medoxomil, candesartan cilexetil, telmisartan, valsartan, and losartan potassium; angiotensin converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate; calcium antagonists such as azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, and manidipin; α-receptor blockers such as tolazoline and phentolamine; β-receptor blockers such as atenolol, metoprolol, acebutolol, propranolol, pindolol, carvedilol, and labetalol hydrochloride; α-receptor stimulants such as clonidine and methyldopa; and diuretics such as eplerenone, hydrochlorothiazide and furosemide.

Exemplary antidiabetics include: α-glucosidase inhibitors such as acarbose, voglibose and miglitol; sulfonylurea hypoglycemic agents such as gliclazide, glibenclamide, glimepiride and tolbutamide; short-acting insulin secretagogues such as nateglinide and mitiglinide; biguanide hypoglycemic agents such as metformin hydrochloride and buformin hydrochloride; dipeptidyl phosphatase-4 inhibitors such as sitagliptin, vildagliptin, alogliptin, linagliptin, teneligliptin, anagliptin and saxagliptin; thiazolidines such as pioglitazone hydrochloride and rosiglitazone maleate; glucagon-like peptide 1 derivatives such as exenatide and liraglutide; and sodium-glucose cotransporter 2 inhibitors such as ipragliflozin, dapagliflozin, luseogliflozin, tofogliflozin, canagliflozin and empagliflozin.

Exemplary antioxidants include such vitamins as ascorbic acid (vitamin C), tocopherol (vitamin E) and tocopherol nicotinate ester, N-acetylcysteine, and probucol.

Exemplary blood flow improving agents include cilostazol, ticlopidine hydrochloride, alprostadil, limaprost, beraprost sodium, sarpogrelate hydrochloride, argatroban, naftidrofuryl, isoxsuprine hydrochloride, batroxobin, dihydroergotoxine mesylate, tolazoline hydrochloride, heproni-cate, and shimotsuto extract.

Exemplary bile acid derivatives include ursodeoxycholic acid, chenodeoxycholic acid, bile powder, deoxycholic acid, cholic acid, bile extract, bear bile, oriental bezoar, and dehydrocholic acid. Favorable examples are biotin (vitamin B7), cyanocobalamin (vitamin B12), pantothenic acid (vitamin B5), folic acid (vitamin B9), thiamine (vitamin B1), vitamin A, vitamin D, vitamin K, tyrosine, pyridoxine (vitamin B6), branched amino acids such as leucine, isoleucine and valine, calcium, iron, zinc, copper, magnesium, and the like. Also favorable are such ingredients of foods for specified health use and foods with nutrient function claims as soybean proteins, chitosan, low molecular-weight sodium alginate, dietary fiber derived from *psyllium* seed husks, soybean peptides bound to phospholipids, plant sterol esters, plant stanol esters, diacylglycerol, globin proteolysis products, and tea catechin.

Exemplary therapeutic agents for NAFLD and NASH include the statins such as pravastatin, simbastatin, atorvastatin, fluvastatin, pitavastatin, rosuvastatin and cerivastatin; the angiotensin II receptor antagonists such as irbesartan, olmesartan medoxomil, candesartan lexetil, telmisartan, valsartan, and losartan potassium; the biguanide hypoglycemic agents such as metformin hydrochloride and buformin hydrochloride; and the thiazolidines such as pioglizone hydrochloride and rosiglitazone maleate as mentioned above, as well as aspirin and farnesoid X receptor (hereafter abbreviated as FXR) ligands such as ursodeoxycholic acid, chenodeoxycholic acid and obeticholic acid.

Exemplary progression suppressants and therapeutic agents for cognitive impairment include acetylcholineesterase inhibitors such as donepezil hydrochloride and galantamine hydrobromide; NMDA receptor inhibitors such as memantine hydrochloride; antiplatelets such as aspirin, clopidogrel sulfate, cilostazol, and ticlopidine hydrochloride; and factor Xa inhibitors such as rivaroxaban and apixaban. In addition, the therapeutic agents for hyperlipidemia, antihypertensives, antidiabetics, antioxidants and blood flow improving agents as mentioned above are also usable as progression suppressants and therapeutic agents for cognitive impairment.

To realize pharmacological actions of the ω3 PUFA, the self-emulsifying composition of the present invention preferably has at least one merit selected from good appearance, good self-emulsifying property, high composition dispersibility, high emulsion stability, high storage stability (including the stability at low and high temperatures), high absorbability, in particular high absorbability and high absorption speed under fasting conditions, and convenience in taking the preparation or compliance.

The self-emulsifying composition of the present invention is well adapted for use as a therapeutic agent for treating various diseases of animals, mammals in particular, that is to say, is usable as, for instance, therapeutic agent for dyslipidemia (hypercholesterolemia, LDL hypercholesterolemia, non-HDL hypercholesterolemia, VLDL hypercholesterolemia, HDL hypocholesterolemia, hypertriglyceridemia, apo B hyperlipoproteinemia, apo A-I hypolipoproteinemia, and so forth), therapeutic agent for postprandial hypertriglyceridemia, anti-arteriosclerotic, platelet aggregation suppressant, therapeutic agent for peripheral circulatory insufficiency, prophylactic agent for cardiovascular events, therapeutic agent for inflammatory disease (NAFLD, NASH, and so forth), progression suppressant and therapeutic agent for cognitive impairment (dementia of the Alzheimer's type, cerebrovascular dementia, mixed type of dementia, and so forth), anticancer agent, and therapeutic agent for central disease (depression, depressive condition, obsessive-compulsive disorder, social anxiety disorder, panic disorder, and so forth). In the treatment of the diseases as above, the inventive self-emulsifying composition is not particularly limited in frequency of administration per day, and is preferably administered one time a day at the entire daily dose or two or three times a day at divided doses, with one or two time administration per day being more preferable and one time administration per day most preferable.

The self-emulsifying composition of the present invention is particularly effective for the amelioration or treatment of dyslipidemia and postprandial hypertriglyceridemia, and the prevention of their recurrence or progression to metabolic syndrome, cardiocerebrovascular events, and ulcer or gangrene at a limb distal end. Exemplary mammals include human, domestic animals such as cattle, horse, and pig, and companion animals such as dog, cat, rabbit, rat, and mouse, and the preferred is human. More specifically, the self-emulsifying composition of the present invention is anticipated to show ameliorating or therapeutic effects for dyslipidemia and postprandial hypertriglyceridemia in patients with dyslipidemia suffering from increase in the blood lipid, exhibiting insulin resistance or suffering from increase in the blood pressure, such as metabolic syndrome patients.

EXAMPLES

Next, the present invention is described in further detail by referring to the following Examples and Comparative Examples which by no means limit the scope of the invention.

Example 1

In a vessel, 0.05 g of water, 0.95 g of polyoxyethylene (20) sorbitan oleate and 4 g of EPA-E as weighed were placed and sealed, and mixed under heating to about 70° C. to thereby prepare a self-emulsifying composition. The self-emulsifying composition thus prepared was sealed after purging with nitrogen, and stored at room temperature until the evaluation was conducted. Formulation of the self-emulsifying composition is shown in Table 1. In the table, the symbol "-" means that the component in question was not added or not measured.

Examples 2 through 8 and Comparative Examples 1 through 3

The self-emulsifying compositions of Examples 2 through 9 and the compositions of Comparative Examples 1 through 3 were prepared and stored by repeating the method of Example 1 so that the compositional ratios were as shown in Table 1. Formulations of the self-emulsifying compositions are shown in Table 1.

Examples 9 through 17 and Comparative Examples 4 through 8

The self-emulsifying compositions of Examples 10 through 15 and the compositions of Comparative Examples 4 through 8 were prepared and stored by repeating the method of Example 1 so that the compositional ratios were as shown in Table 2. Formulations of the self-emulsifying compositions are shown in Table 2.

Test Example 1

Evaluation of Appearance

The self-emulsifying compositions and the compositions of Comparative Examples as produced by the above production method were allowed to stand at room temperature, and after about 1 hour, their appearance was evaluated. When the composition was homogeneous due to its good compatibility, the composition was evaluated as "transparent." The composition was evaluated as "separated" when the separation was observed, and "cloudy" when opacity was observed.

The results are shown in Tables 1 and 2.

Test Example 2

Evaluation of Self-emulsifying Property

The self-emulsifying compositions and the compositions of Comparative Examples as produced by the above production method were evaluated for self-emulsifying property by adding 10 μL of each composition dropwise to 5 mL of purified water or first fluid for dissolution test of Japanese Pharmacopeia at 37° C. in the test tube. The composition which spontaneously emulsified just by the dropwise addition was evaluated as "good," and the case which did not become an emulsion just by the dropwise addition was evaluated as "poor." The composition was then lightly stirred under consistent condition, and other properties were examined. With regard to the dispersibility of the composition, the composition was evaluated as "good" when dispersed and as "poor" when partly left undispersed as a mass. With regard to the emulsion stability, the composition was evaluated as "good" when no oil separation was observed, and as "poor" when oil separation was observed. It is to be noted that the compositions which were not evaluated as "transparent" in the appearance evaluation were not evaluated in such properties since inhomogeneous compositions were conceived to be inadequate for property evaluation.

The results are shown in Tables 1 and 2.

Test Example 3

Evaluation of Emulsion Droplet Diameter
Conditions for the Measurement of Mean Droplet Diameter and Measurement Results Using about 1.5 mL of the emulsified composition as obtained in Test Example 2, the mean droplet diameter (volume mean diameter) was measured by a particle size analyzer (Nanotrac, manufactured by Nikkiso Co., Ltd.) using water as a dispersion medium.

The results are shown in Tables 1 and 2.

Test Example 4

Evaluation of the Appearance after Storage Under Severe Conditions

The compositions which were evaluated as "transparent" in Test Example 1 were allowed to stand and stored overnight (for about 12 hours) at 5° C. or 40° C. before their appearance was evaluated. When the composition was homogeneous due to its good compatibility, the composition was evaluated as "transparent." The composition was evaluated as "separated" when the separation was observed, and as "cloudy" when opacity was observed.

The results are shown in Tables 1 and 2. In the tables, the symbol "-" means that the component in question was not added or not measured.

TABLE 1

| Component | Ex. 1 | Ex. 2 | Ex. 3 | Ex. 4 | Ex. 5 | Ex. 6 | Ex. 7 | Ex. 8 | Comp. Ex. 1 | Comp. Ex. 2 | Comp. Ex. 3 |
|---|---|---|---|---|---|---|---|---|---|---|---|
| Ethyl eicosapentaenoate | 80.0 | 84.0 | 80.0 | 75.0 | 84.0 | 80.0 | 80.0 | 76.0 | 80.0 | 80.0 | 94.0 |
| Purified water | 1.0 | 1.0 | 1.0 | 2.0 | 1.0 | 1.0 | 0.5 | 4.0 | 0.0 | 8.0 | 1.0 |
| Polyoxyethylene (20) sorbitan oleate | 19.0 | 8.6 | 10.0 | — | 7.0 | 17.0 | 10.5 | 10.0 | 10.0 | 7.0 | 5.0 |
| Polyoxyethylene (20) sorbitan trioleate | — | — | — | 15.0 | — | — | — | — | — | — | — |
| Sorbitan monolaurate | — | — | — | — | 3.0 | — | 4.0 | 5.0 | 5.0 | 2.0 | — |
| Sorbitan sesquioleate | — | 6.4 | — | — | — | — | 1.0 | — | — | — | — |
| Decaglyceryl oleate | — | — | 9.0 | — | — | — | — | — | — | — | — |
| Polyoxyl 35 castor oil | — | — | — | 8.0 | 4.0 | — | 4.0 | 5.0 | 5.0 | 3.0 | — |
| Propylene glycol fatty acid ester | — | — | — | — | 1.0 | — | — | — | — | — | — |
| Soybean lecithin | — | — | — | — | — | 2.0 | — | — | — | — | — |
| Total | 100.00 | 100.00 | 100.00 | 100.00 | 100.00 | 100.00 | 100.00 | 100.00 | 100.00 | 100.00 | 100.00 |

| | | Ex. 1 | Ex. 2 | Ex. 3 | Ex. 4 | Ex. 5 | Ex. 6 | Ex. 7 | Ex. 8 | Comp. Ex. 1 | Comp. Ex. 2 | Comp. Ex. 3 |
|---|---|---|---|---|---|---|---|---|---|---|---|---|
| Test Ex. 1 | Appearance | Transparent | Transparent | Transparent | Transparent | Transparent | Transparent | Transparent | Transparent | Separated | Separated | Separated |
| Test Ex. 2 | Self-emulsifying property | Good | Good | Good | Good | Good | Good | Good | Good | Not evaluated | Not evaluated | Not evaluated |
| | Composition dispersibility | Good | Good | Good | Good | Good | Good | Good | Good | | | |
| | Emulsion stability | Good | Good | Good | Good | Good | Good | Good | Good | | | |
| Test Ex. 3 Emulsion droplet diameter | 37° C. Purified water (μm) | 0.23 | 0.41 | 0.19 | 0.19 | 0.22 | 0.25 | 0.21 | 0.20 | | | |
| | 37° C. Japanese Pharmacopeia 1st liquid (μm) | 0.29 | 0.29 | 0.87 | 0.24 | 0.18 | 0.27 | 0.18 | 0.23 | | | |
| Test Ex. 4 Appearance | Stored at 5° C. | Transparent | Transparent | Transparent | Transparent | Transparent | Transparent | Transparent | Transparent | | | |
| | Stored at 40° C. | Transparent | Transparent | Transparent | Transparent | Transparent | Transparent | Transparent | Transparent | | | |

TABLE 2

| Component | Ex. 9 | Ex. 10 | Ex. 11 | Ex. 12 | Ex. 13 | Ex. 14 | Ex. 15 | Ex. 16 | Ex. 17 |
|---|---|---|---|---|---|---|---|---|---|
| Ethyl eicosapentaenoate | 75.0 | 80.0 | 80.0 | 82.0 | 84.0 | 80.0 | 84.0 | 80.0 | 80.0 |
| Purified water | 2.0 | 2.0 | 1.0 | 1.0 | 1.0 | 1.0 | 1.0 | 1.0 | 1.0 |
| Polyoxyethylene (20) sorbitan oleate | — | — | — | — | 10.0 | 10.0 | 8.0 | 10.0 | 10.0 |
| Sorbitan monolaurate | — | 7.5 | 5.0 | 5.0 | 4.0 | 4.0 | 4.0 | 4.0 | — |
| Sorbitan sesquioleate | — | — | — | — | — | — | — | — | — |
| Sorbitan monooleate | — | — | — | — | — | — | — | — | 4.0 |
| Glyceryl monooleate | — | — | — | — | — | — | — | 1.0 | — |
| Decaglyceryl oleate | 15.0 | — | 9.0 | 7.0 | 8.0 | — | — | — | — |
| Polyoxyl 35 castor oil | 8.0 | 10.5 | 5.0 | 5.0 | 3.0 | 5.0 | 3.0 | 5.0 | 5.0 |

TABLE 2-continued

| | | | | | | | | | | |
|---|---|---|---|---|---|---|---|---|---|---|
| Soybean lecithin | — | — | — | — | — | — | — | — | — | |
| Propylene glycol | — | — | — | — | — | — | — | — | — | |
| Ethanol | — | — | — | — | — | — | — | — | — | |
| Total | 100.00 | 100.00 | 100.00 | 100.00 | 100.00 | 100.00 | 100.00 | 100.00 | 100.00 | |

| | | Ex. 9 | Ex. 10 | Ex. 11 | Ex. 12 | Ex. 13 | Ex. 14 | Ex. 15 | Ex. 16 | Ex. 17 |
|---|---|---|---|---|---|---|---|---|---|---|
| Test Ex. 1 | Appearance | Transparent | Transparent | Transparent | Transparent | Transparent | Transparent | Transparent | Transparent | Transparent |
| Test Ex. 2 | Self-emulsifying property | Good | Good | Good | Good | Good | Good | Good | Good | Good |
| | Composition dispersibility | Good | Good | Good | Good | Good | Good | Good | Good | Good |
| | Emulsion stability | Good | Good | Good | Good | Good | Good | Good | Good | Good |
| Test Ex. 3 Emulsion droplet diameter | 37° C. Purified water (μm) | 0.18 | 0.25 | 0.22 | 0.29 | 0.29 | 0.18 | 0.18 | 0.21 | 0.21 |
| | 37° C. Japanese Pharmacopeia 1st liquid (μm) | 0.18 | 0.34 | 0.22 | 0.25 | 0.26 | 0.29 | 0.17 | 0.22 | 0.27 |
| Test Ex. 4 Appearance | Stored at 5° C. | Transparent | Transparent | Transparent | Transparent | Transparent | Transparent | Transparent | Transparent | Transparent |
| | Stored at 40° C. | Transparent | Transparent | Transparent | Transparent | Transparent | Transparent | Transparent | Transparent | Transparent |

| Component | Comp. Ex. 4 | Comp. Ex. 5 | Comp. Ex. 6 | Comp. Ex. 7 | Comp. Ex. 8 |
|---|---|---|---|---|---|
| Ethyl eicosapentaenoate | 80.0 | 75.2 | 70.0 | 80.0 | 80.0 |
| Purified water | — | — | — | — | 1.0 |
| Polyoxyethylene (20) sorbitan oleate | — | 5.8 | — | 11.4 | — |
| Sorbitan monolaurate | 7.5 | — | 14.3 | — | — |
| Sorbitan sesquioleate | — | — | — | 8.6 | — |
| Sorbitan monooleate | — | — | — | — | — |
| Glyceryl monooleate | — | — | — | — | — |
| Decaglyceryl oleate | — | — | — | — | — |
| Polyoxyl 35 castor oil | 10.5 | 5.8 | 15.7 | — | 19.0 |
| Soybean lecithin | — | 6.5 | — | — | — |
| Propylene glycol | — | 6.7 | — | — | — |
| Ethanol | 2.0 | — | — | — | — |
| Total | 100.00 | 100.00 | 100.00 | 100.00 | 100.00 |

| | | Comp. Ex. 4 | Comp. Ex. 5 | Comp. Ex. 6 | Comp. Ex. 7 | Comp. Ex. 8 |
|---|---|---|---|---|---|---|
| Test Ex. 1 | Appearance | Separated | Transparent | Transparent | Transparent | Separated |
| Test Ex. 2 | Self-emulsifying property | Not evaluated | Good | Good | Good | Not evaluated |
| | Composition dispersibility | | Good | Good | Good | |
| | Emulsion stability | | Good | Good | Good | |
| Test Ex. 3 Emulsion droplet diameter | 37° C. Purified water (μm) | | 0.18 | 0.17 | 0.68 | |
| | 37° C. Japanese Pharmacopeia 1st liquid (μm) | | 0.18 | 0.48 | 0.33 | |
| Test Ex. 4 Appearance | Stored at 5° C. | | Transparent | Precipitated | Separated | |
| | Stored at 40° C. | | Separated | Transparent | Separated | |

The composition of Example 1 contained a polyoxyethylene sorbitan fatty acid ester as the only emulsifier together with a specified amount of water, and, as shown in Table 1, had good appearance and excellent properties including self-emulsifying property. This result indicates that the merits of the present invention are realized even by a composition only containing a polyoxyethylene sorbitan fatty acid ester as an emulsifier.

The compositions of Examples 2 through 8 and 14 through 17 had various emulsifiers added thereto apart from the polyoxyethylene sorbitan fatty acid ester as an emulsifier, and further contained water. The compositions were excellent in appearance, self-emulsifying property and other properties, as was the case with the composition of Example 1.

The compositions of Examples 7 and 8 as well as Comparative Examples 1 and 2 contained water in varied amounts. The composition of Comparative Example 1 contained no water, and became separated. The composition of Comparative Example 2, which contained 8% by weight of water, also became separated.

In the present invention, water is used instead of ethanol or a polyhydric alcohol in order to improve the compatibility of a composition. The composition having contained no water was separated due to its inadequate compatibility. At the same time, the composition with too high a water content was also separated. Separation did not occur in the compositions of Examples 1 through 9 each having contained 0.5 to 4% by weight of water. These results indicate that addition of water in a specified amount of about 0.5% to about 6% by weight is important in preparing the inventive composition which is excellent in appearance and properties.

The composition of Comparative Example 3, which contained water and had a high ethyl eicosapentaenoate content of 94% by weight, became separated. It is considered that even a composition containing the specified amount of water will be separated if it has an oil content higher than 70 to 90% by weight because the amount of emulsifiers containable is reduced relative to the amount of oil components.

The composition of Comparative Example 4 contained no water but ethanol, and separation was observed in its appearance evaluation.

The composition of Example 10 was prepared by replacing the ethanol as used in Comparative Example 4 by water, and was good in appearance. It is considered that, in the case of water, a content of about 2% by weight can bring about an adequate compatibility, while separation occurred in the composition of Comparative Example 4 having contained 2% by weight of ethanol due to the shortage of ethanol.

The composition of Comparative Example 5 contained no water but lecithin and a polyhydric alcohol. As in the case of Example 1 and the like, this composition had good appearance and excellent properties including self-emulsifying property at room temperature.

The composition, however, was separated after overnight storage at 40° C., which demonstrates that addition of the specified amount of water allows a composition of good appearance even in the environment at higher or lower temperatures.

The compositions of Examples 9 through 13 each contained at least two emulsifiers selected from among a sorbitan fatty acid ester, a glycerin fatty acid ester and a polyoxyl castor oil, and further contained water. As shown in Table 2, the compositions had good appearance and were excellent in self-emulsifying property and other properties.

On the other hand, the composition of Comparative Example 8, which contained only one selected from among the above emulsifiers, had a separated appearance. The results indicate that two or more emulsifiers need to be selected.

The compositions of Comparative Examples 5 through 7 each contained emulsifiers selected from among a polyoxyethylene sorbitan fatty acid ester, a sorbitan fatty acid ester and a polyoxyl castor oil, and contained no water. Although the compositions were transparent in appearance at room temperature, separation or precipitation occurred in the compositions during the storage at lower and/or higher temperatures because of their not containing water.

The composition of Comparative Example 8 only contained a polyoxyl castor oil as an emulsifier, and became separated at temperatures of 5° C. and 40° C. In the present invention, in order to obtain the self-emulsifying composition which has good performance if containing the specified amount of water, it is necessary to use, as an emulsifying agent, i) a polyoxyethylene sorbitan fatty acid ester or ii) at least two emulsifiers selected from among a sorbitan fatty acid ester, a glycerin fatty acid ester and a polyoxyethylene castor oil. It is seen from this Comparative Example that the use of a polyoxyethylene castor oil alone does not allow the self-emulsifying composition as expected. In other words, it has been found that a certain emulsifier or emulsifying agent needs to be used for the self-emulsifying composition which has good performance if containing the specified amount of water.

Test Example 5

Pharmacokinetics in Beagles

The composition of Example 14 was orally administered to 6 male beagles (at the age of 2 to 6 years with the body weight of 13 kg, 3 Marshall beagles and 3 Nosan beagles) under fasting conditions, and blood EPA concentration was evaluated. The test animals had been fasted since 18 hours or more before the administration, and each animal was administered with the composition in an amount corresponding to 600 mg of the EPA-E. Blood was collected before the administration, and 0.5, 1, 1.5, 2, 3, 4, 6, 8, and 24 hours after the administration, and plasma was separated to measure plasma EPA concentration by LC/MS/MS (method in which a sample is isolated by liquid chromatography, then subjected to mass spectrometry to conduct separation and measurement thereon). The control group was administered with the EPA-E stock solution encapsulated in a capsule.

Table 3 shows the maximum blood concentration (Cmax), the area under the blood concentration vs time curve from zero to two hours ($AUC_{0-2}$) and the area under the blood concentration vs time curve from zero to 24 hours ($AUC_{0-24}$) as calculated from the test results. In the calculation of each parameter, correction was made by subtracting the blood EPA concentration before the administration from the measured blood concentration.

TABLE 3

| Results of Test Ex. 5 | Ex. 14 (Fasted) | EPA-E Stock solution (Control fasted) |
|---|---|---|
| Cmax (μg/mL) | 120.7 | 16.6 |
| $AUC_{0-2}$ (μg/mL · hr) | 84.0 | 14.4 |
| $AUC_{0-24}$ (μg/mL · hr) | 844.6 | 188 |

In the animals as administered with the self-emulsifying composition of Example 14, values of the Cmax and the $AUC_{0-2}$, which are parameters of the absorption speed, were higher than the control group (fasted). With respect to the $AUC_{0-2}$ which is in particular a parameter of the blood concentration increase immediately after the administration, the values in the animals as administered with the composition of Example 14 were about six times as high as those in the control group. The Cmax values were about 7.3 times as high as those in the control group. On the other hand, with respect to the $AUC_{0-24}$ as a parameter of the absorption amount, the values in the animals as administered with the self-emulsifying composition of Example 14 were about 4.5 times as high as those in the control group. More specifically, it was confirmed that, when the self-emulsifying composition of Example 14 was administered, amount of the EPA absorbed until 24 hours after the oral administration increased, and also, EPA absorption was rapid especially after the oral administration compared to the control group. Accordingly, the self-emulsifying composition of the present invention would be a candidate for the self-emulsifying preparation capable of rapidly and markedly increasing the blood EPA concentration with rapid and effective pharmacological action even if taken under pre-meal, pre-sleeping, or other fasting conditions.

Test Example 6

Pharmacokinetics in Crab-eating Macaques

The composition of Example 14 is orally administered to 6 crab-eating macaques (at the age of 2 to 5 years with the body weight of 2.70 to 4.65 kg; Hamuri) under fasting conditions, and blood EPA concentration is evaluated. The test animals are fasted for 12 hours or more before the administration, and each animal is administered with the self-emulsifying composition in an amount corresponding to 45 mg/kg body weight of the EPA-E. The control group is administered with the EPA-E stock solution encapsulated in a capsule. Blood is collected before the administration, and 1, 2, 4, 6, 8, 10, 12, 24, 48 and 72 hours after the administration, and plasma is separated to measure EPA in plasma by LC/MS/MS. From the test results, the maximum blood concentration (Cmax), the area under the blood concentration vs time curve from zero to 12 hours ($AUC_{0-12}$), and the area under the blood concentration vs time curve from zero to 72 hours ($AUC_{0-72}$) are calculated. In the calculation of each parameter, correction is made by subtracting the blood EPA concentration before the administration from the measured blood concentration.

In the animals having the composition of Example 14 administered thereto, values of blood concentration parameters, such as the Cmax and the $AUC_{0-12}$, are increased as compared with the control group. More specifically, it is confirmed that, when the self-emulsifying composition of Example 14 is administered, amount of the EPA absorbed is increased, and also, EPA absorption is rapid after the oral administration.

Example 2-1

Self-emulsifying Capsule Preparation

A soft gelatin capsule filled with 375 mg (amount corresponding to 300 mg of EPA-E) of the self-emulsifying composition as obtained in Example 14 was produced by rotary method. The self-emulsifying capsule preparation thus produced was identical in shape to the soft gelatin capsule as filled with EPA-E alone, and escaped from such disadvantages as the deformation of capsule film immediately after the production.

Referential Example 2-2 and Comparative Example 2-3

Capsule Preparations

The self-emulsifying composition of the Example and the composition of the Comparative Example were prepared and stored by repeating the method of Example 1 so that the compositional ratios were as shown in Table 4. Formulations of the compositions are shown in Table 4.

A soft gelatin capsule filled with 375 mg of the composition of Comparative Example 2-1 and that filled with 441 mg of the composition of Comparative Example 2-2 (both amounts corresponding to 300 mg of EPA-E) were produced by rotary method. The self-emulsifying capsule preparation thus produced was identical in shape to the soft gelatin capsule as filled with EPA-E alone, and escaped from such disadvantages as the deformation of capsule film.

Test Example 6

Capsule Hardness Retention

The capsule preparations of Example 2-1, Referential Example 2-2 and Comparative Example 2-3 were measured in hardness. Each preparation was also measured in hardness after the storage at 40° C. and a relative humidity of 75%; for one, two, and four weeks.

The results at the initial stage and the results after the storage at 40° C. for one, two, and four weeks are shown in Table 4. The preparation at the initial stage refers to the preparation which has been stored at room temperature after its production until the evaluation of the hardness. Since having been stored at 40° C. as sealed in aluminum packages, the preparations were not affected by the moisture.

TABLE 4

| Component | | Ex. 2-1 | Referential Ex. 2-2 | Comparative Ex. 2-3 |
|---|---|---|---|---|
| Ethyl eicosapentaenoate | | 80.0 | 80.0 | 68.0 |
| Purified water | | 1.0 | 2.0 | — |
| Polyoxyethylene (20) sorbitan oleate | | 10.0 | 5.8 | 7.1 |
| Sorbitan monolaurate | | 4.0 | — | — |
| Polyoxyl 35 castor oil | | 5.0 | 5.8 | 7.1 |
| Soybean lecithin | | — | 6.4 | 9.5 |
| Propylene glycol | | — | — | 8.3 |
| Total | | 100.0 | 100.0 | 100.0 |
| Test Ex. 6 Hardness (kgf) | Initial stage | 31.8 | 28.9 | 15.7 |
| | At 40° C. for 1 week | — | — | 9.1 |
| | At 40° C. for 2 weeks | 31.1 | — | 8.9 |
| | At 40° C. for 4 weeks | 30.8 | 27.4 | 8.1 |

The preparation of Example 2-1 is a capsule preparation of the present invention, and the preparation of Referential Example 2-2 is of a formulation replacing sorbitan monolaurate contained in Example 2-1 by soybean lecithin. The preparations had hardness values of 31.8 kgf and 28.9 kgf, respectively, at the initial stage, values very close to each other, and such values were essentially not reduced even after the storage at 40° C. for one to four weeks. This indicates that neither a sorbitan fatty acid ester nor soybean lecithin is a component causing the reduction in hardness of a capsule.

The preparation of Comparative Example 2-3 is of a formulation replacing water in Referential Example 2-2 by propylene glycol. The hardness of this preparation was about 54% of that of Referential Example 2-2, that is to say, the preparation was inferior in hardness already at the initial stage. Moreover, the hardness of the preparation was greatly reduced after the storage at 40° C. for only one week.

It was found from the above that, while a polyhydric alcohol possibly comprising about 8% of the liquid content will cause the reduction in hardness, the inventive composition that contains no polyhydric alcohols but water does not cause the reduction in hardness.

INDUSTRIAL APPLICABILITY

The self-emulsifying composition of the present invention is excellent in at least one out of the compatibility (appearance), the self-emulsifying property, the composition dispersibility, the emulsion stability and the absorbability, and it, as being absorbed rapidly even if taken before meals, suppresses increase of serum TG after the meal. The self-emulsifying composition of the present invention is useful for incorporating in various foods, or as food for special dietary uses, food with health claims (food for specified health use and food with nutrient function claims), health food (supplement), or a pharmaceutical product.

The self-emulsifying composition of the present invention has no or low content of the polyhydric alcohol, and therefore, the composition is free from the problem of softening and deformation of the capsule during the distribution or storage caused by the polyhydric alcohol. In other words, the self-emulsifying composition of the present invention is associated with reduced risk of quality change.

The self-emulsifying composition of the present invention has the quality as a pharmaceutical product capable of being stored in a cold or hot location since the composition does not become cloudy or separated even if stored in low or high temperature environment.

The invention claimed is:

1. A self-emulsifying composition comprising, when the self-emulsifying composition is defined to be 100% by weight as a whole,
   a) 70 to 90% by weight of at least one compound selected from the group consisting of ω3 polyunsaturated fatty acids and their pharmaceutically acceptable salts and esters,
   b) 0.5 to 6% by weight of water, and
   c) 1 to 29% by weight of an emulsifying agent including either
      i) a polyoxyethylene sorbitan fatty acid ester or
      ii) at least two members selected from the group consisting of a sorbitan fatty acid ester, a glycerin fatty acid ester and a polyoxyethylene castor oil, or
   1 to 29% by weight of an emulsifying agent including
      i) a polyoxyethylene sorbitan fatty acid ester and
      ii) at least one member selected from the group consisting of a sorbitan fatty acid ester, a glycerin fatty acid ester and a polyoxyethylene castor oil, wherein
   d) content of ethanol is up to 4% by weight of the whole composition, and
   e) content of polyhydric alcohol is up to 4% by weight of the whole composition,
   wherein the composition is free from separation and cloudiness and maintains good appearance when stored at a temperature of 5° C. for 12 hours or at a temperature of 40° C. for 12 hours.

2. The self-emulsifying composition according to claim 1, wherein the ω3 polyunsaturated fatty acids and their pharmaceutically acceptable salts and esters include at least one member selected from the group consisting of EPA, DHA, and their pharmaceutically acceptable salts and esters.

3. The self-emulsifying composition according to claim 1, wherein the polyhydric alcohol is propylene glycol or glycerin.

4. The self-emulsifying composition according to claim 1, wherein the content of the ethanol is up to 1% by weight of the whole composition.

5. The self-emulsifying composition according to claim 1, wherein the content of the polyhydric alcohol is up to 1% by weight of the whole composition.

6. The self-emulsifying composition according to claim 1, wherein said self-emulsifying composition further comprises lecithin, wherein a content of lecithin in the composition is less than 3 parts by weight in relation to 100 parts by weight of the at least one compound selected from the group consisting of ω3 polyunsaturated fatty acids and their pharmaceutically acceptable salts and esters.

7. A capsulated self-emulsifying preparation having a self-emulsifying composition held in a capsule as a liquid content, with the self-emulsifying composition comprising, when the self-emulsifying composition is defined to be 100% by weight as a whole,
   a) 70 to 90% by weight of at least one compound selected from the group consisting of ω3 polyunsaturated fatty acids and their pharmaceutically acceptable salts and esters,
   b) 0.5 to 6% by weight of water, and
   c) 1 to 29% by weight of an emulsifying agent including either
      i) a polyoxyethylene sorbitan fatty acid ester or
      ii) at least two members selected from the group consisting of a sorbitan fatty acid ester, a glycerin fatty acid ester and a polyoxyethylene castor oil, or
   1 to 29 % by weight of an emulsifying agent including
      i) a polyoxyethylene sorbitan fatty acid ester and
      ii) at least one member selected from the group consisting of a sorbitan fatty acid ester, a glycerin fatty acid ester and a polyoxyethylene castor oil,
   and having
   d) an ethanol content which is up to 4% by weight of the whole composition, and
   e) a polyhydric alcohol content which is up to 4% by weight of the whole composition,
   wherein the capsule is a hard capsule and/or a soft capsule,
   wherein the composition is free from separation and cloudiness and maintains good appearance when stored at a temperature of 5° C. for 12 hours or at a temperature of 40° C. for 12hours.

8. The capsulated self-emulsifying preparation according to claim 7, wherein a capsule film of the soft capsule contains gelatin.

9. The self-emulsifying composition according to claim 2, wherein the polyhydric alcohol is propylene glycol or glycerin.

10. The self-emulsifying composition according to claim 9, wherein the content of the ethanol is up to 1% by weight of the whole composition.

11. The self-emulsifying composition according to claim 10, wherein said self-emulsifying composition further comprises lecithin, wherein a content of lecithin in the composition is less than 3 parts by weight in relation to 100 parts by weight of the at least one compound selected from the group consisting of ω3 polyunsaturated fatty acids and their pharmaceutically acceptable salts and esters.

12. The self-emulsifying composition according to claim 2, wherein said self-emulsifying composition further comprises lecithin, wherein a content of lecithin in the composition is less than 3 parts by weight in relation to 100 parts by weight of the at least one compound selected from the group consisting of ω3 polyunsaturated fatty acids and their pharmaceutically acceptable salts and esters.

* * * * *